US009388338B2

(12) United States Patent
Li et al.

(10) Patent No.: US 9,388,338 B2
(45) Date of Patent: *Jul. 12, 2016

(54) LIQUID CRYSTAL MIXTURE

(75) Inventors: Ji Li, Kakegawa (JP); Toshiaki Nonaka, Kakegawa (JP); Ayako Ogawa, Kakegawa (JP); Hans-Rolf Dübal, Eltville (DE); Barbara Hornung, Hasselroth (DE); Wolfgang Schmidt, Dreieich (DE); Rainer Wingen, Hattersheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/201,605

(22) Filed: Aug. 11, 2005

(65) Prior Publication Data

US 2006/0011886 A1 Jan. 19, 2006

Related U.S. Application Data

(62) Division of application No. 10/363,009, filed as application No. PCT/EP01/09832 on Aug. 25, 2001, now Pat. No. 6,958,176.

(30) Foreign Application Priority Data

Aug. 30, 2000 (EP) .................................... 00118736

(51) Int. Cl.
| | |
|---|---|
| *C07D 211/46* | (2006.01) |
| *C09K 19/34* | (2006.01) |
| *C09K 19/54* | (2006.01) |
| *C07D 211/04* | (2006.01) |
| *C09K 19/58* | (2006.01) |
| *C09K 19/02* | (2006.01) |
| *C07D 211/06* | (2006.01) |
| *C07D 211/08* | (2006.01) |
| *C07D 211/18* | (2006.01) |

(52) U.S. Cl.
CPC .............. *C09K 19/54* (2013.01); *C07D 211/04* (2013.01); *C07D 211/46* (2013.01); *C09K 19/3483* (2013.01); *C09K 19/58* (2013.01); *C07D 211/06* (2013.01); *C07D 211/08* (2013.01); *C07D 211/18* (2013.01); *C09K 19/0225* (2013.01); *C09K 19/0266* (2013.01); *Y10T 428/10* (2015.01)

(58) Field of Classification Search
CPC .. C07D 211/46; C07D 211/04; C07D 211/06; C07D 211/08; C07D 211/18; C09K 19/3483; C09K 19/54; C09K 19/58; C09K 19/0225; C09K 19/0266
USPC ................. 428/1.1; 252/299.01, 299.2, 299.5
See application file for complete search history.

(56) References Cited

U.S. PATENT DOCUMENTS

| | | | | |
|---|---|---|---|---|
| 3,663,558 A | * | 5/1972 | Murayama | 546/249 |
| 3,847,930 A | * | 11/1974 | Randell | 546/344 |
| 3,937,711 A | * | 2/1976 | Cook | 546/247 |
| 3,939,168 A | * | 2/1976 | Cook | 546/233 |
| 3,954,779 A | | 5/1976 | Smith et al. | |
| 4,038,280 A | * | 7/1977 | Randell et al. | 546/240 |
| 4,153,596 A | * | 5/1979 | Oertel et al. | 525/375 |
| 4,537,698 A | * | 8/1985 | Sucrow et al. | 252/299.61 |
| 5,384,065 A | | 1/1995 | Geelhaar et al. | |
| 5,851,682 A | * | 12/1998 | Kotani et al. | 428/500 |
| 6,506,462 B1 | | 1/2003 | Tarumi et al. | |
| 6,824,707 B2 | * | 11/2004 | Amakawa et al. | 252/299.01 |
| 6,958,176 B2 | * | 10/2005 | Li et al. | 428/1.1 |
| 8,349,210 B2 | * | 1/2013 | Xu et al. | 252/299.01 |
| 2003/0127627 A1 | | 7/2003 | Amakawa et al. | |

FOREIGN PATENT DOCUMENTS

| | | |
|---|---|---|
| DE | 2258086 A1 | 6/1973 |
| DE | 2415818 A1 | 10/1974 |
| DE | 19629812 A1 | 2/1997 |
| DE | 19927492 A1 | 12/1999 |
| DE | 19857352 A1 | 6/2000 |
| EP | 0385688 A2 | 9/1990 |
| EP | 0474062 A2 | 3/1992 |
| GB | 849282 A * | 9/1960 |
| GB | 2338489 A | 12/1999 |

(Continued)

OTHER PUBLICATIONS

CAPLUS 1980: 542033.*
Derwent abstract for JP 55023169, 1980.*
English abstract for JP 55-023169, 1980.*
English abstract for JP 11021325, 1999.*
CA 130: 169282, 1999.*
CAPLUS 1976:165540.*
CAPLUS 1977: 16523.*
CAPLUS 1961: 4332.*
CAPLUS 1974: 505204.*
CAPLUS 1984: 51408.*

(Continued)

*Primary Examiner* — Shean C Wu
(74) *Attorney, Agent, or Firm* — Millen White Zelano and Branigan, PC; Csaba Henter; Anthony Zelano

(57) ABSTRACT

Liquid crystal mixture comprising one or several compounds of formula (I)

$$R^1-N\underset{R^5\ R^6}{\overset{R^3\ R^4}{\bigcirc}}-M^1-(A)_m-M^2-R^2 \quad (I)$$

wherein $R^1$, $R^2$, $R^3$, $R^4$, $R^5$, $R^6$, $M^1$, $M^2$, X, A, and m are defined herein.

30 Claims, No Drawings

(56) References Cited

FOREIGN PATENT DOCUMENTS

| JP | 55-23169 | * | 2/1980 |
|---|---|---|---|
| JP | 58168641 A2 | | 10/1983 |
| JP | 11021325 | * | 2/1999 |
| JP | 5117324 B2 | | 1/2013 |
| SU | 435235 A1 | | 7/1974 |
| SU | 631516 A1 | | 11/1978 |

OTHER PUBLICATIONS

CAPLUS 1973: 479797.*
CAPLUS 2002: 326791, 2002.*
CAPLUS 1960: 70020.*
CAPLUS 1975: 171926.*
CAPLUS 1972: 565545.*
CAPLUS 1973: 454269.*
English Abstract of JP 58168641 published on Oct. 5, 1983.
Database CAPLUS'Online!, Chemical Abstracts Service, Columbus, OH, Hirabayashi: "Photographic material showing good colorability and forming color image with excellent lightfastness", 1999.
Database CA 'Online!, Chemical Abstracts Service, Columbus, OH, Shapro, A. B. et al, "Dipiperidine derivatives", 1974.
Wilen, C-E, et al, "preparation of hindered piperidine and its copolymerization", 1992.
Database CA 'Online!, Chemical Abstracts Service, Columbus, OH, Pavlikov, V. V. et al, "New polyyne derivatives of 2,2,6,6-tetramethylpiperidin-1-oxyl", 1980.
Hartman, W.J.A.M, "Ferroelectric Liquid-Crystal Video Display", 1989.
Okumura, H., et al., "A 15-in XGA TFT-AFLCD with quasi-dc driving scheme for montor applications", 1998.
Nito, K., et al, "A novel surface-stabilized monostable ferroelectric LCD", 1993.
Furue, H., et al., "Monostable polymer-stabilized SSFLCD with high contrast ratio and grayscale capability", 1998.
Takahashi T., et al., "Preliminary study of field sequential fullcolor liquid crystal display using polymer stabilized ferroelectric liquid crystal display", 1999.
Nonaka, T., et al., "Material characteristics of an active matrix LCD based upon chiral smectics", 1999.
Sasaki, A., et al., "3.1-Invited, Active addressing for flat panel display", 1986.
Nakazono, Y., et al., "Characterization of LC materials with negative dielectric anisotrophy for active matrix LCDS", 1997.
Fukuoka, N., et aL, "DC offset voltage in liquid crystal cells", 1994.
Takatoh, K., "The application of (a) FLC materials to AM-LCD's", 1997.
Takatoh, K., et al., "Application of FLC/AFLC materials to active-matrix devices", 2000.
Petrov, V., "Liquid crystals for advanced display applications", 1995.
Dabrowski, R., "Liquid crystalline materials for active matrix displays", 1999.
Kirsch, P., et al., "Nematic liquid crystals for active matrix displays: molecular design and synthesis", 2000.
Kiefer, R., et al., "In-plane switching of nematic liquid crystals", 1992.
Ohmuro, K., et al., "33.3: Development of super-high-image-quality vertical-alignment-mode LCT", 1997.
Clark, Noel, et al, "Submicrosecond bistable eletro-optic switching in liquid crystals", 1980.
Nagata, Seiichi, et al., "14.5: Capacitively Coupled Driving of TFT-LCD", 1989.
Dagonneau, M., et al., "Chemistry of hindered amines from the piperidine series", 1984.
Rozantsev, E.G., et al., "Discovery, chemistry and application of hindered amines", 1985.
Skowronski, Romuald, et al.,"Synthesis of some 4-substituted 4-hydroxy-2,6,6-tetramethylpiperidines and their nitroxyl radicals", 1980.
Hall, Patricia L., et al., "Mixed aggregation of lithium emulates and lithium halides with lithium 2,2,6,6-tetramethylpiperidide (LTMP)", 1991.
Tsukuda, T., "TFT/LCD liquid crystal displays addressed by thin film transistors", 1996.
English abstract for SU 435235, Aug. 31, 1993.
English abstract for SU 631516, Sep. 1, 1993.
English abstract for DE 19857352, Jun. 15, 2000.
English abstract for RO 92779, Sep. 23, 1993.
XP-002157538, English abstract for JP 5117324, May 14, 1993.
XP-002157537, English abstract for JP 55023169, Feb. 19, 1980.
XP-002157539, English abstract for JP 11174642, Jul. 2, 1999.

* cited by examiner

LIQUID CRYSTAL MIXTURE

CROSS-REFERENCE TO RELATED APPLICATION

This application is a continuation application of Ser. No. 10/363,009, filed Feb. 26, 2003, the contents of which are hereby incorporated herein by reference; which is the National Stage of International Application No. PCT/EP01/09832, filed Aug. 25, 2001, the contents of which are hereby incorporated herein by reference; which claims priority to European Patent Application No. 00118736.8, filed Aug. 30, 2000, the contents of which are hereby incorporated herein by reference.

The present invention relates to a novel liquid crystal mixture. More particularly, it relates to a chiral smectic or ferroelectric liquid crystal mixture, which is chemically very stable against heat and light, thus being especially suitable for active matrix panels. A further aspect of this invention is the use of this liquid crystal mixture in displays, especially active matrix displays. Yet another aspect of this invention are active matrix displays comprising such a mixture.

Since Clark and Lagerwall found Surface Stabilized Ferroelectric Liquid Crystals (SSFLC) in 1980 [N. A. Clark and S. T. Lagerwall, Appl. Phys. Lett., 36, 899 (1980)], these liquid crystals have attracted attentions as display materials in the coming generation and a number of studies have been carried out thereon.

There are two major advantages of FLC displays: the 'pixel speed' is easily 100 or even 1000 times faster than nematics and secondly, due to the bistability, the resolution of such displays is not limited by the material.

However, passive matrix FLC displays are limited by certain trade-off relationships: the higher the number of scanning lines, the higher is the frame addressing time and thus the speed of a display is always in competition with its resolution.

With respect to the trade-offs of passive matrix FLC displays several authors have suggested to combine the active matrix with FLC. The first approach was made by Hartmann (IEEE Trans. Electron. Devices 1989, 36(9), part 1, pp. 1895-9) in the 80s utilising the charge-controlled bistability of a quasi-bookshelf FLC with MOS-FET technology. The large Ps values, however, prohibited higher resolution with a-Si TFT driving.

Takatoh et. al. (6$^{th}$ International Conference on Ferroelectric Liquid Crystals, 1997, 20-24 Jul., Brest, France; M. Takatoh et al. 1998, SID Digest, 1171-1174) have demonstrated an AM display based upon chiral smectics using a very high $P_S$ material driven with an active matrix with polycrystalline Silicon-TFT. Nito et. al. (Nito et al., 1993, Journal of the SID, 1/2, 163-169) have suggested a monostable AM-FLC with much lower $P_S$, however, with the disadvantage of a stripey FLC texture which is not suitable for high contrast displays without further improvements. Furue et. al. (Furue, H. et al., 1998, IDW '98, 209-212) suggested a polymer stabilized SSFLCD with a FELIX® mixture with a material having a moderate $P_S$ value.

High $P_S$-values require long charge-up times on each of the pixels and are therefore incompatible with high resolution, i.e. a large number of scanning lines. This is the reason why Takatoh et. al. have used a special poly-crystalline silicon active matrix that allows for higher current densities as compared to the standard and cost-effective amorphous silicon TFT.

Asao et. al. have presented a monostable FLC mode (Y. Asao et al., ILCC 2000, Sendai, and Jpn. J. Appl. Phys. 38, L534-L536, 1999 therein called "half-V-shape FLC" mode; see also T. Nonaka et. al., Liquid Crystals 26(11), 1599-1602, 1999, therein called "CDR" mode). Such displays provide, by virtue of their smaller $P_S$ values, solutions for the gray scale problem and the resolution limitation caused by too large $P_S$ values in active matrix panels.

A remaining problem in the application of TFT-LCD (e.g. monostable FLC) is the limited "holding ratio", caused by the activity of the manifold of charge carriers that are present in the pixel volume and which tend to discharge the pixel within too short a time. In particular for the fast switching displays with a very thin cell gap the problem of ionic charges which build up depolarisation fields leads to significant limitations (cp. Sasaki, Japan Display 1986, 62; Nakazono, Int. Dev. Res. Cent. Techn. Rep. IDRC 1997, 65; Naemura, SID Dig. Techn. Pap. 1989, 242; Fukuoka, AM LCD 1994, 216; Takatori, AM-LCD 97 DIGEST 1997, 53; Takatoh, Polym. Adv, Technol. 11, 413 (2000)).

Thus it is an important factor to maintain a very low ion content and to achieve chemical stability against heat and light, both of which could cause additional ion formation. This demand has in practice lead to the exclusion of any material comprising hetero atoms such as N, S, even O in liquid crystal mixtures for active matrix (i.e. TFT or MIM) applications {cp. e.g. Petrov et al., Liq. Cryst. 19(6), 729 (1995) [CAN 124:101494]; Petrov, Proc. SPIE-Int. Soc. Opt. Eng. (1995), 2408 [CAN 123:241500]; Dabrowski, Biul. Wojsk. Akad. Techn. 48(4), 5 (1999) [CAN 131:163227]; Kirsch, Angew. Chem., Int. Ed. 39(23), 4216 (2000) and references cited in these papers}. Whereas, so far, this could successfully be done for nematics (cp. e.g. DE-A 1 962 9812, p. 12 to 16), there is hardly any smectic ($S_c$) material without such hetero atoms (cp. Demus et al., Flüssige Kristalle in Tabellen, vol. 1 and 2). Thus the use of fast switching smectics for TFT application is strongly limited if not prohibited and the range of potentially available nematics is strongly reduced.

The object of the present invention was therefore to provide a liquid crystal mixture with very high resistivity or holding ratio irrespective of the comprisment of hetero atoms, especially a chiral smectic, in particular ferroelectric or antiferroelectric liquid crystal mixtures which are suitable for active matrix panels, especially with respect to withstanding heat- or light-induced chemical stress while maintaining the performance of a low-ion-content mixture.

The present invention provides a liquid crystal mixture, especially a chiral smectic mixture, in particular a ferroelectric or antiferroelectric liquid crystal mixture, most particularly a monostable ferroelectric liquid crystal mixture comprising one or several compounds of formula (I)

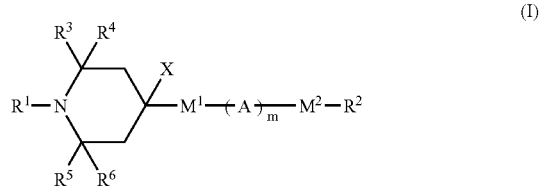

(I)

wherein
$R^1$: is H or a linear or branched alkyl group of 1 to 20 C atoms or linear or branched alkenyl group of 2 to 20 C atoms, wherein in either case one —$CH_2$— group can be replaced by cyclohexylen-1,4-diyl, or one or two —$CH_2$— groups can be replaced by —O—, if non-adjacent to N, or by —C(=O)— or —Si(CH$_3$)$_2$—, and one or more H of the alkyl or alkenyl group optionally being replaced by F or CH$_3$.

R$^2$: stands for
a) H or F
b) a linear or branched alkyl group of 1 to 20 C atoms or linear or branched alkenyl group of 2 to 20 C atoms, wherein in either case one or two —CH$_2$— groups can be replaced by —O—, —C(=O)O—, —Si(CH$_3$)$_2$—, it also being possible to replace one or more H of the alkyl or alkenyl group by F or CH$_3$.
c) for a radical

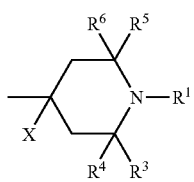

wherein independently from the respective meanings in (I)
R$^3$, R$^4$, R$^5$, R$^6$: represent independently from another an alkyl group of 1 to 8 C atoms
M$^1$, M$^2$ stand: independently from another for a single bond, —OC(=O), —C(=O)O—, —OCH$_2$—, or —NH—
A: is
a) a linear or branched alkan-α,ω-diyl group of 1 to 20 or alkene-α,ω-diyl group of 2 to 20 C atoms, it also being possible to replace, if non-adjacent to M$^{1/2}$, one or two non-adjacent —CH$_2$— groups by —O—
b) the group —C(=Y)— wherein Y is CH—Z with Z being phenylen-1,4-diyl, optionally substituted by 1 to 3 halogen atoms, alkyl or alkyloxy groups of 1 to 4 C atoms, with the proviso that M$^1$ and M$^2$ are —C(=O)O— and —OC(=O)—, respectively;
c) the group —CHY wherein Y is CH$_2$—Z with Z being phenylen-1,4-diyl, optionally substituted by 1 to 3 halogen atoms, alkyl or alkyloxy groups of 1 to 4 C atoms, with the proviso that M$^1$ and M$^2$ are —C(=O)O— and —OC(=O)—, respectively
d) a group

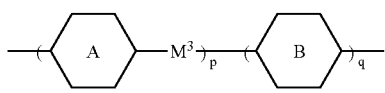

wherein
p, q are 0, 1 or 2, and the sum of p+q being ≥1
M$^3$ is a single bond, —OC(=O)—, —C(=O)O—, —OCH$_2$—, —CH$_2$O—, —C≡C—, —CH$_2$CH$_2$—, —CH$_2$CH$_2$CH$_2$CH$_2$—
the radicals

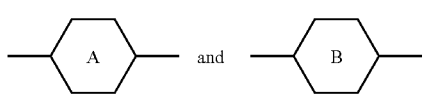

are independently from another phenylen-1,4-diyl, which optionally can be substituted by one, two or three F, or cyclohexan-1,4-diyl, which can optionally be substituted by one CN, CH$_3$ or F, or pyrimidin-2,5-diyl, optionally substituted by one F, pyridine-2,5-diyl, which can optionally be substituted by one F, or naphthalene-2,6-diyl, which can optionally be substituted by one, two or three F, or 1,2,3,4-tetrahydronaphthalene-2,6-diyl (the aromatic ring optionally substituted by one, two or three F), or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol-2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl X is H, OH, or a linear or branched alkyl or alkyloxy group of 1 to 20 C atoms, wherein one or two —CH$_2$— groups can be replaced by —O—, —C(=O)O—, —Si(CH$_3$)$_2$—, it also being possible to replace one or more H by F or CH$_3$
m: is 0 or 1
X and M$^1$-(A)$_m$-M$^2$-R$^2$ together can constitute
a) a ring of 4 to 16 members, optionally substituted by alkyl of 1 to 15 C atoms b) a combination of two either directly linked or spiro-linked rings of independently from another 4 to 16 members, optionally substituted by alkyl of 1 to 15 C atoms in either of the three variants the rings are independently from another carbocycles or carbocycles comprising B, N, O or S heteroatoms. Preferably the mixtures comprise 0.01 wt.-% to 10 wt.-% of one or several compounds of formula (I).

Especially preferred are mixtures comprise 0.1 wt.-% to 5 wt.-% of one or several compounds of formula (I).

Preferably the mixtures comprise one or several compounds of the following formulae

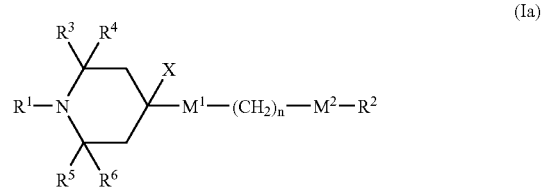

wherein
X is H
R$^1$ is H or alkyl of 1 to 4 C atoms
R$^3$, R$^4$, R$^5$, R$^6$ are CH$_3$
and/or

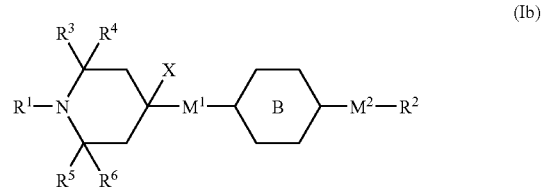

wherein
X is H
R$^1$ is H or alkyl of 1 to 4 C atoms
R$^3$, R$^4$, R$^5$, R$^6$ are CH$_3$ and/or

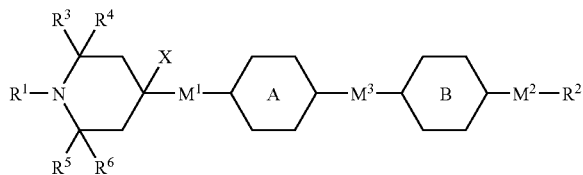
(Ic)

wherein
X is H
R¹ is H or alkyl of 1 to 4 C atoms
R³, R⁴, R⁵, R⁶ are CH₃
and/or

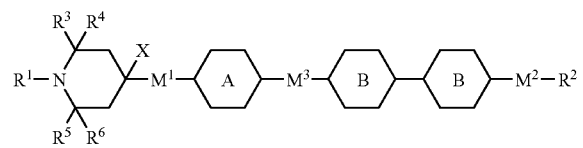
(Id)

wherein
X is H
R¹ is H or alkyl of 1 to 4 C atoms
R³, R⁴, R⁵, R⁶ are CH₃.

Particularly preferred are mixtures comprising

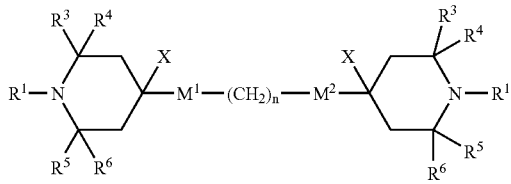
(Ia1)

wherein
X is H
R¹ is H or alkyl of 1 to 4 C atoms
R³, R⁴, R⁵, R⁶ are CH₃
M¹ is —OC(=O)—
M² is —C(=O)O—
n is 4 to 12
and/or

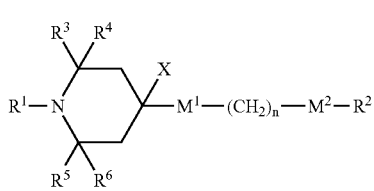
(Ia2)

wherein
X is H
R¹ is H or alkyl of 1 to 4 C atoms
R³, R⁴, R⁵, R⁶ are CH₃

R² is H
M¹ is —OC(=O)—
M² is a single bond
n is 8 to 20
and/or

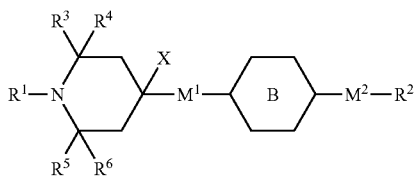
(Ib1)

wherein
X is H
R¹ is H or alkyl of 1 to 4 C atoms
R³, R⁴, R⁵, R⁶ are CH₃
R² is H or an alkyl or alkyloxy group of 1 to 16 C atoms, wherein one or two —CH₂— groups can be replaced by —O—, —OC(=O)—, —Si(CH₃)₂—, it also being possible to replace one or more H by F or CH₃
M¹ is —OC(=O)—
M² is a single bond

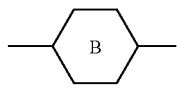

is phenylen-1,4-diyl, optionally substituted by one or two F, or cyclohexylen-1,4-diyl, pyrimidine-2,5-diyl, pyridine-2,5-diyl
and/or

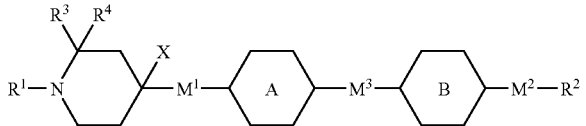
(Ic1)

wherein
X is H
R¹ is H or alkyl of 1 to 4 C atoms
R³, R⁴, R⁵, R⁶ are CH₃
R² is H or an alkyl or alkyloxy group of 1 to 16 C atoms, wherein one or two —CH₂— groups can be replaced by —O—, —OC(=O)—, —Si(CH₃)₂—, it also being possible to replace one or more H by F or CH₃
M¹ is —OC(=O)—
M² is a single bond
M³ is a single bond, —OC(=O)—, —OCH₂—

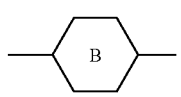

is phenylen-1,4-diyl, optionally substituted by one or two F, or cyclohexylen-1,4-diyl, pyrimidine-2,5-diyl, or pyridine-2,5-diyl

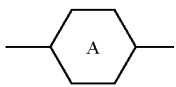

is phenylen-1,4-diyl, optionally substituted by one or two F, or cyclohexylen-1,4-diyl, pyrimidine-2,5-diyl, or pyridine-2,5-diyl
and/or

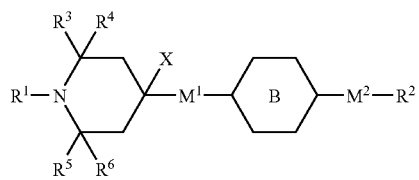
(Ib2)

wherein
X is H
$R^1$ is H or alkyl of 1 to 4 C atoms
$R^3, R^4, R^5, R^6$ are $CH_3$
$R^2$ is H or an alkyl or alkyloxy group of 1 to 16 C atoms, wherein one or two —$CH_2$— groups can be replaced by —O—, —OC(=O)—, —Si(CH$_3$)$_2$—, it also being possible to replace one or more H by F or $CH_3$
$M^1$ is a single bond
$M^2$ is a single bond ![B ring]

is phenylen-1,4-diyl, optionally substituted by one or two F, or cyclohexylen-1,4-diyl,
and/or ![Ic2 structure]
(Ic2)

wherein
X is H
$R^1$ is H or alkyl of 1 to 4 C atoms
$R^3, R^4, R^5, R^6$ are $CH_3$
$R^2$ is H or an alkyl or alkyloxy group of 1 to 16 C atoms, wherein one or two —$CH_2$— groups can be replaced by —O—, —OC(=O)—, —Si(CH$_3$)$_2$—, it also being possible to replace one or more H by F or $CH_3$
$M^1$ is a single bond
$M^2$ is a single bond
$M^3$ is a single bond ![B ring]

is phenylen-1,4-diyl, optionally substituted by one or two F, or cyclohexylen-1,4-diyl, ![A ring]

Several compounds of the formula (I) are commercially available. The synthesis of the not commercially available compounds of formulae (I) and (II), resp., or new compounds of formulae (I), (II), (III) and (IV), resp., are performed in analogy to pertinent papers, e.g. Dagonneau et al., Synthesis 1984, pp. 895-916 [CAN 103:37294]; Rozantsev et al., ACS Symp. Ser. (1985), 280 (Polym. Stab. Degrad), pp. 11-35 [CAN 103:142668].

In particular the commercially available 2,2,6,6-tetramethylpiperidine-4-one and 4-hydroxy-2,2,6,6-tetramethylpiperidine can serve as precursors for the new compounds of formulae (I), (II), (III) and (IV).

E.g. (Ia), wherein $M^1$ and $M^2$ are single bonds, $R^2$ an alkyl group of 1 to 20 C atoms, can be obtained by reacting 2,2,6,6-tetramethyl-4-piperidone with an alkyl magnesium halide to render 4-alkyl-4-hydroxy-2,2,6,6-tetramethyl-piperidine (in analogy to Skowronski et al., Pol. J. Chem. 54, 195, 1980)), dehydration to 3,4-dehydro-4-alkyl-2,2,6,6-tetramethylpiperidine [corresponds to formula (IV)] and consecutive hydrogenation (e.g. in analogy to DE-A 2258086). Alternatively Wittig reagents can be applied for the first step (e.g. in analogy to Collum et al., J. Am. Chem. Soc. 113, 9575 (1991)).

E.g. (Ia), wherein $M^1$ is —OC(=O)—, can be obtained by subjecting 4-hydroxy-2,2,6,6-tetramethylpiperidine to esterification (in analogy to U.S. Pat. No. 4,038,280, Example 14) with an appropriate carboxylic acid derivative X—C(=O)(CH$_2$)-M$^2$-R$^2$ (X: Cl, Br or OH).

E.g. (Ia1), wherein $M^1$ is —OC(=O)— and $M^2$ is —C(=O)O—, can be obtained by subjecting 4-hydroxy-2,2,6,6-tetramethylpiperidine to esterification (in analogy to U.S. Pat. No. 4,038,280, Example 14) with an appropriate carboxylic acid derivative X—C(=O)(CH$_2$)C(=O)X (X: Cl, Br or OH).

E.g. (Ib), wherein $M^1$ is a single bond, $M^2$ is —OCH$_2$—, R an alkyl group of 1 to 20 C atoms and ![B ring]

is phenylen-1,4-diyl, can be obtained by bringing into reaction 2,2,6,6-tetramethyl-piperidine-4-one and phenol (in analogy to SU 631 516; CA 90:54839) to render 3,4-dehydro-4-(4-hydroxyphenyl)-2,2,6,6-tetramethyl-piperidine, which is hydrogenated to 4-(4-hydroxyphenyl)-2,2,6,6-tetramethyl-piperidine (in analogy to DE-A-2 258 086). This material can be (in analogy to U.S. Pat. No. 4,038,280, Example 25) transferred to the above mentioned examples of (Ib) by reacting with an appropriate alkyl halide X—$R^2$ (X: Halide, Tosylate, Mesylate; $R^2$ not H or F).

E.g. (Ib), wherein $M^1$ is a single bond, $M^2$ is —OC(=O)—, $R^2$ an alkyl group of 1 to 20 C atoms and

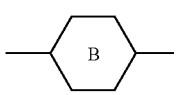

is phenylen-1,4-diyl, can be obtained from above mentioned 4-(4-hydroxyphenyl)-2,2,6,6-tetramethyl-piperidine by esterification with an appropriate carboxylic acid derivative X—C(=O)—$R^2$ (X: Cl, Br, OH; R not H or F) (e.g. in analogy to U.S. Pat. No. 4,038,280, Example 14).

E.g. (Ib), wherein $M^1$ is a single bond, $M^2$ is —OC(=O)— or —OCH$_2$—, $R^2$ an alkyl group of 1 to 20 C atoms and

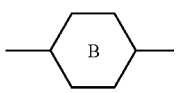

is cyclohexyl-1,4-diyl, can be obtained from above mentioned 4-(4-hydroxyphenyl)-2,2,6,6-tetramethyl-piperidine by hydrogenation (in analogy to DE-A-2 415 818) to 4-(4-hydroxycyclohexyl)-2,2,6,6-tetramethyl-piperidine and consecutive etherification with an appropriate alkyl halide X—$R^2$ (X: Halide, Tosylate, Mesylate; $R^2$ not H or F) or esterification with an appropriate carboxylic acid derivative X—C(=O)—$R^2$ (X: Cl, Br, OH; $R^2$ not H or F) (e.g. in analogy to U.S. Pat. No. 4,038,280, Example 14 and 25), resp.

E.g. (Ic), wherein $M^1$ is a single bond, $M^3$ is —OC(=O)—, $R^2$ H, F or an alkyl group of 1 to 20 C atoms,

is phenylen-1,4-diyl or cyclohexyl-1,4-diyl and

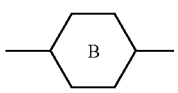

is phenylen-1,4-diyl, optionally substituted by one, two or three F, or cyclohexyl-1,4-diyl, optionally substituted by one CN, CH$_3$ or F, or pyrimidin-2,5-diyl, pyridin-2,5-diyl, naphthalin-2,6-diyl, optionally substituted by one, two or three F, thiophen-2,4-diyl, thiophen-2,5-diyl, can be obtained by subjecting above mentioned 4-(4-hydroxy-phenyl)-2,2,6,6-tetramethyl-piperidine and 4-(4-hydroxycyclohexyl)-2,2,6,6-tetramethyl-piperidine, respectively, to esterification with a moiety (X: F, Cl, Br or OH) (e.g. in analogy to U.S. Pat. No. 4,038,280, Example 14).

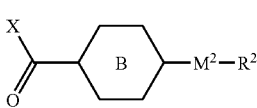

E.g. (Ic), wherein $M^1$ is a single bond, $M^3$ is —OCH$_2$—,

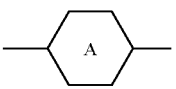

is phenylen-1,4-diyl or cyclohexyl-1,4-diyl and

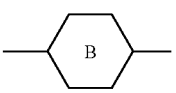

is phenylen-1,4-diyl, optionally substituted by one, two or three F, or cyclohexyl-1,4-diyl, optionally substituted by one CN, CH$_3$ or F, or pyrimidin-2,5-diyl, pyridin-2,5-diyl, naphthalin-2,6-diyl, optionally substituted by one, two or three F, or thiophen-2,4-diyl, thiophen-2,5-diyl, can be obtained by subjecting (in analogy to U.S. Pat. No. 4,038,280, Example 25) above mentioned 4-(4-hydroxyphenyl)-2,2,6,6-tetramethyl-piperidine and 4-(4-hydroxycyclohexyl)-2,2,6,6-tetramethyl-piperidine, respectively, to etherification with a moiety (X: Cl, Br, Tosylate, Mesylate)

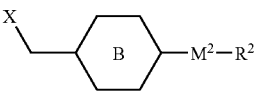

E.g. (Ic), wherein $M^1$ is a single bond, $M^3$ is a single bond, $R^2$ H, F or an alkyl group of 1 to 20 C atoms,

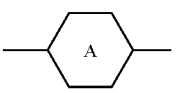

is phenylen-1,4-diyl or cyclohexyl-1,4-diyl and

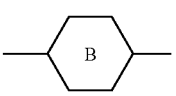

is phenylen-1,4-diyl, optionally substituted by one, two or three F, or cyclohexyl-1,4-diyl, optionally substituted by one CN, CH$_3$ or F, or pyrimidin-2,5-diyl, pyridin-2,5-diyl, naphthalin-2,6-diyl, optionally substituted by one, two or three F, thiophen-2,4-diyl, thiophen-2,5-diyl, can be obtained by subjecting above mentioned 4-(4-hydroxy-phenyl)-2,2,6,6-tetramethyl-piperidine and 4-(4-hydroxycyclohexyl)-2,2,6,6-tetramethyl-piperidine, respectively, after transformation into an appropriate derivate (e.g. triflate), to an aryl-(cyclohexyl-)-aryl coupling reaction {Poetsch, Kontakte (Darmstadt), 1988 (2), p. 15)} with a moiety (X: ClMg—, BrMg—, IMg—, Li—, ClZn—, (HO)$_2$B—).

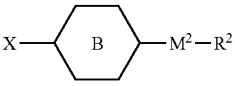

E.g. (Id) can be obtained in analogy to (Ic), in all the variants given above.

A further object of the invention is to provide compounds of formula (II) and a nematic liquid crystal mixture comprising at least one compound of formula (I) or (II). Preferably the mixture comprises 0.05 to 5% of one or several compounds of formula (I) and/or (II). Especially preferred are mixtures comprising 0.05 to 5% of one or several compounds of formula (II).

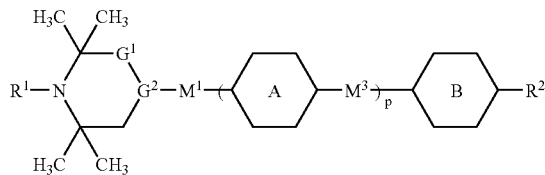

wherein
$R^1$ is H or alkyl of 1 to 12 C atoms
$R^2$ is H, a linear or branched alkyl group of 1 to 16 or linear or branched alkenyl group of 2 to 16 C atoms, wherein in either case one —$CH_2$— group can be replaced by —O—, it also being possible to replace one or more H by F
$M^1$ is —OC(=O)— or a single bond
$M^3$ is a single bond
$G^1$-$G^2$ is —$CH_2$—CH— or —CH=C—
p is 0 or 1

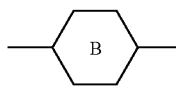

is phenylen-1,4-diyl, optionally substituted by one or two F, cyclohexylen-1,4-diyl, biphenyl-4,4'-diyl, optionally substituted by one or two F per ring, 1,1'-cyclohexyl-phenyl-4,4'-diyl, the phenyl moiety optionally substituted by one or two F, or 1,1'-phenylcyclohexyl-4,4'-diyl, the phenyl moiety optionally substituted by one or two F, or 1,1'-bicyclohexyl-4,4'-diyl

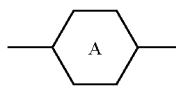

is phenylen-1,4-diyl, optionally substituted by one or two F, or cyclohexylen-1,4-diyl,
with the proviso
a) $R^2$ is H only in case p is 1
b) if p is 0, than $R^2$ is a linear or branched alkyl group of 1 to 16 or linear or branched alkenyl group of 2 to 16 C atoms and

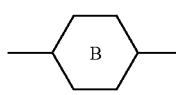

is cyclohexylen-1,4-diyl
c) -$G^1$-$G^2$- can be —CH=C— only in case $M^1$ is a single bond A further object of the invention is to provide compounds of formula (III) and a chiral smectic liquid crystal mixture comprising at least one compound of formula (III). Preferably the mixture comprises 0.05 to 5% of one or several compounds of formula (III).

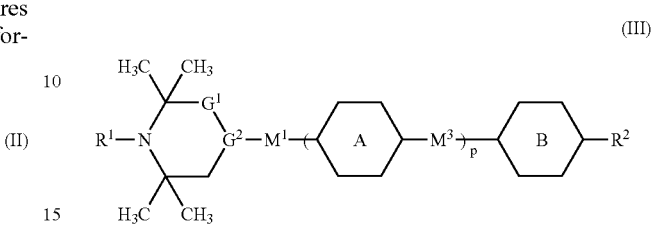

wherein
$R^1$ is H or alkyl of 1 to 12 C atoms
$R^2$ is H, a linear or branched alkyl group of 1 to 16 or linear or branched alkenyl group of 2 to 16 C atoms, wherein in either case one —$CH_2$— group can be replaced by —O—, it also being possible to replace one or more H by F
$M^1$ is —OC(=O)— or a single bond
$M^3$ is a single bond
$G^1$-$G^2$ is —$CH_2$—CH— or —CH=C—
p is 0 or 1

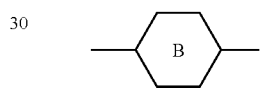

is pyrimidin-2,5-diyl, pyridin-2,5-diyl, optionally ortho to N substituted by F, phenylen-1,4-diyl, optionally substituted by one or two F, or cyclohexylen-1,4-diyl, biphenyl-4,4'-diyl, optionally substituted by one or two F per ring, 1,1'-cyclohexylphenyl-4,4'-diyl, the phenyl moiety optionally substituted by one or two F, or 1,1'-phenylcyclohexyl-4,4'-diyl, the phenyl moiety optionally substituted by one or two F, or 1,1'-bicyclohexyl-4,4'-diyl

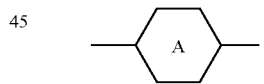

is phenylen-1,4-diyl, optionally substituted by one or two F, cyclohexylen-1,4-diyl, biphenyl-4,4'-diyl, optionally substituted by one or two F per ring, 1,1'-cyclohexylphenyl-4,4'-diyl, the phenyl moiety optionally substituted by one or two F, or 1,1'-phenylcyclohexyl-4,4'-diyl, the phenyl moiety optionally substituted by one or two F, or 1,1'-bicyclohexyl-4,4'-diyl, pyrimidin-2,5-diyl, or pyridin-2,5-diyl, optionally ortho to N substituted by F,
with the provisos
a) one and only one of

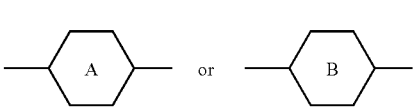

or is pyrimidin-2,5-diyl or pyridin-2,5-diyl, optionally ortho to N substituted by F b) -G$^1$-G$^2$- can be —CH=C— only in case M$^1$ is a single bond Yet another object of the invention is to provide a liquid crystal mixture comprising at least 1 compound of formula (IV)

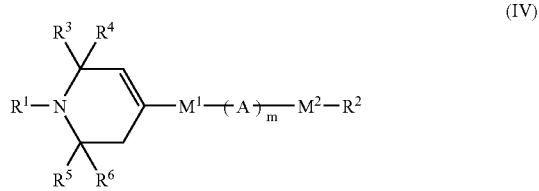

(IV)

wherein R$^1$ to R$^6$, A, M$^2$ and m have the meanings as in formula (I) and M$^1$ is a single bond.

A further object of the invention is to provide a liquid crystal display device, especially one operated in an active matrix panel using the above described mixtures.

A further object of the invention is to provide a chiral smectic liquid crystal display device, especially one operated in an active matrix panel using the above described mixtures.

A further object of the invention is to provide a ferroelectric liquid crystal display device, especially one operated in an active matrix panel using the above described mixtures. With preference this display is a monostable ferroelectric display, such as half-V-shape, CDR or short pitch FLC displays.

A further object of the invention is to provide an antiferroelectric liquid crystal display device, especially one operated in an active matrix panel using the above described mixtures. With preference this display is a monostable antiferroelectric display, such as the so-called "V-shape" mode.

A further object of the invention is to provide a nematic liquid crystal display device, especially one operated in an active matrix panel using the above described mixtures.

Yet a further object of the invention is the use of the above described mixtures in a liquid crystal display, especially one operated in an active matrix panel, especially if the liquid crystal is a chiral smectic, particularly a monostable chiral smectic mode.

The liquid crystal mixtures according to the invention are prepared in a manner which is customary per se. As a rule the components are dissolved in one another, advantageously at elevated temperatures.

The liquid crystal mixtures according to the invention generally comprises of at least two (2), preferably at least five (5), particularly at least eight (8) compounds.

Reference is made to e.g. DE-A-1 985 7352 or DE-A 1 962 9812 (p. 12 to 16) for the LC compounds that can be, besides the compounds of formula (I), (II), (III) or (IV), the constituents of mixtures according to the invention.

Optional additional constituents of the mixtures according to invention are materials that increase the light stability (UV stabilizers, e.g. of the "benzophenone" or "benzotriazole" type). Preferably the mixtures may comprise 0.01 wt.-% to 10 wt.-% of one or several UV stabilizers; especially preferred are mixtures containing 0.1 wt.-% to 5 wt.-% of one or several UV stabilizers.

Optional additional constituents of the mixtures according to invention are materials that increase the stability against oxidative degradation (antioxidants, e.g. of the "sterically hindered phenol" type). Preferably the mixtures may comprise 0.01 wt.-% to 10 wt.-% of one or several antioxidants; especially preferred are mixtures comprise 0.1 wt.-% to 5 wt.-% of one or several antioxidants.

Optionally the mixtures according to invention may comprise a combination of UV stabilizers and antioxidants.

The mixtures according to the invention can be used in electro-optical or fully optical elements, for example display elements, switching elements, light modulators, shutters, elements for image processing and/or signal processing or generally in the area of nonlinear optics.

Chiral smectic liquid crystal mixtures according to the invention are particularly suitable for use in electro-optical switching and display devices (displays). These displays are usually constructed in such a way that a liquid crystal layer is enclosed on both sides by layers which are usually, in this sequence starting from the LC layer, at least one alignment layer, electrodes and a limiting sheet (for example of glass). In addition, they contain spacers, adhesive frames, polarizers and, for color displays, thin color-filter layers or are operated in the sequential backlight technique. Other possible components are antireflection, passivation, compensation and barrier layers and, for active-matrix displays, electric non-linear elements, such as thin-film transistors (TFTs) and metal-insulator-metal (MIM) elements. The structure of liquid crystal displays has already been described in detail in relevant monographs (see, for example, T. Tsukuda, "TFT/LCD Liquid crystal displays addressed by thin film transistors", Japanese Technology Reviews, 1996 Gordon and Breach, ISBN 2-919875-01-91.

The present invention further provides a chiral smectic liquid crystal (FLC) display device comprising the above-mentioned liquid crystal mixture of the present invention between a pair of substrates each comprising an electrode and an alignment layer formed thereon.

In a preferred embodiment the FLC display is operated in the monostable mode with active matrix panel.

The present invention further provides a nematic liquid crystal display device comprising the above-mentioned liquid crystal mixture of the present invention between a pair of substrates each comprising an electrode and an alignment layer formed thereon. In a preferred embodiment the display is operated in the ECB mode (EP-A 0474062). IPS mode (Kiefer et al., Japan Display '92, S.547) or VA mode (Ohmura et al., SID 97 Digest, S.845).

Several documents are cited in this application, e.g. to discuss the state of the art, synthesis of compounds used in the present invention or application of the mixtures according to the invention. All these documents are hereby incorporated by reference.

EXAMPLES

Cell Fabrication

A solution of LQT 120 (Hitachi Kasei) is applied onto glass substrates with ITO by spin coating at 2500 rpm. The substrates are heated at 200° C. for 1 hour to form a film. After rubbing the coated film with a nylon cloth in one direction, the substrates are assembled into a cell with spacers having a thickness of 2.0 μm inserted between the substrates in such a manner that the rubbing directions are anti-parallel to each other. The properties of the liquid crystal mixture are measured by filling the liquid crystal mixture into the cell in the isotropic phase, cooling progressively through the nematic, (smectic A phase in case the liquid crystal mixture has one) and the smectic C phase and then applying a rectangular wave pulse (60 Hz) with varying applied voltage (0 to 10V) to the cell at 25° C.

Resistivity and ion-induced spontaneous polarization are measured by means of a MTR-1 device (Toya Technica).

Table 1 summarizes the results thus obtained by adding small quantities of several types of (I) to $S_c$ mixture A and B, respectively. As can be seen by comparing with the respective reference examples rA/rB {comprising no (I)}, the mixtures according to invention surprisingly exhibit a higher resisitivity and decreased ion content. Hence the mixtures according to invention can find application in active-matrix devices.

TABLE 1

| ex. | | | Mixture A | | | Mixture B | | |
|---|---|---|---|---|---|---|---|---|
| | | | wt.-% | Resistivity [TΩcm] | Ion Cont. [nC/cm²] | wt.-% | Resistivity [TΩcm] | Ion Cont. [nC/cm²] |
| rA/rB | Without (I) | Trade Name | 0 | 8.5 | 0.44 | 0 | 7.1 | 2.3 |
| 1A 1B | 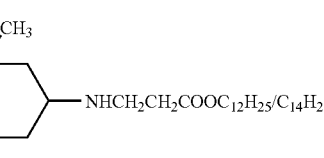 | Sanduvor 3052 Liq. | 0.1 | >10 | <0.1 | 0.1 | 7.22 | 0.24 |
| 2A 2B | 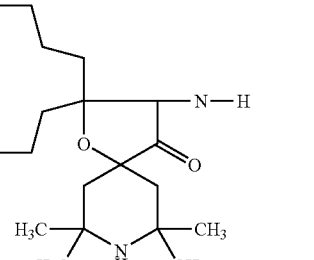 | Hostavin N20 (Sanduvor 3051 PDR) | 0.1 | >10 | <0.1 | 0.1 | >10 | 0.25 |
| 3A 3B | 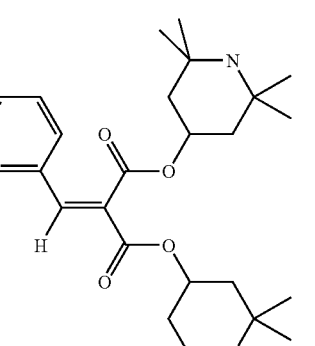 | VP Sanduvor PR-31 | 0.1 | >10 | <0.1 | 0.1 | 3 | 0.24 |
| 4A 4B | 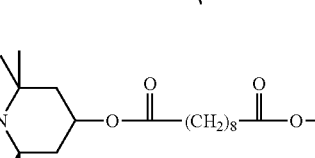 | TINUVIN 765 | 1.0 | >10 | <0.1 | 1.0 | 8.4 | 0.15 |
| 5A 5B | 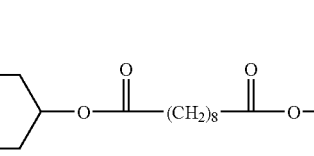 | TINUVIN 770 | 1.0 | >10 | <0.1 | 1.0 | 8.2 | 0.18 |

TABLE 1-continued

| ex. | | Mixture A | | | Mixture B | | |
|---|---|---|---|---|---|---|---|
| | | wt.-% | Resistivity [TΩcm] | Ion Cont. [nC/cm$^2$] | wt.-% | Resistivity [TΩcm] | Ion Cont. [nC/cm$^2$] |
| 6A 6B | with n = 13 to 16 | LICOVIN 845 0.1 | >10 | <0.1 | 0.1 | 8.0 | <0.1 |

Example 7

2,2,6,6-Tetramethyl-piperidine-4-(4-octyloxy)benzoate was obtained by esterifying 4-hydroxy-2,2,6,6-tetramethyl-piperidine with 4-octyloxybenzoyl chloride in analogy to U.S. Pat. No. 4,038,280; m.p. 79-81° C.

Example 8

2,2,6,6-Tetramethyl-piperidine-4-(4'-octyl-biphenyl-4-yl) carboxylate) was obtained in analogy to example 7 from 4'-octyl-biphenyl-4-yl carboxylic acid chloride; m.p. 104-106° C.

Example 9

2,2,6,6-Tetramethyl-piperidine-4-(trans-4-pentylcyclohexyl)carboxylate was obtained in analogy to example 7 from trans-4-pentylcyclohexyl)carboxylic acid chloride; viscous liquid, crystallizes on standing (m.p. 44 to 48° C.).

Example 10

2,2,6,6-Tetramethyl-piperidine-4-[4-(trans-4-propylcyclohexyl)]benzoate was obtained in analogy to example 7 from 4-(trans-4-propylcyclohexyl)benzoyl chloride.

Example 11

2,2,6,6-Tetramethyl-piperidine-4-[4-(5-hexyl-pyrimidin-2-yl)]benzoate was obtained in analogy to example 7 from 4-(5-hexyl-pyrimidin-2-yl)benzoylchloride.

Example 12

2,2,6,6-Tetramethyl-piperidine-4-[4'-(4-decyloxy)benzoyloxy-biphenyl-4-yl]carboxylate was obtained in analogy to example 7 from [4'-(4-decyloxy)benzoyloxy-biphenyl-4-yl]carboxylic acid chloride.

Example 13

2,6,6-Tetramethyl-piperidine-4-(4-hexyl)benzoate was obtained in analogy to RO 92779 B1 (CAN 109:171562) by heating a xylene solution of methyl 4-hexylbenzoate, 4-hydroxy-2,2,6,6-tetramethylpiperidine and sodium methanolate to reflux for 10 hrs. Silica treatment and recrystallization rendered pure material of m.p. 61-62° C.

Example 14

2,2,6,6-Tetramethylpiperidine-4-(4'-heptylbiphenyl-4-yl) carboxylate was obtained in analogy to example 13 by subjecting methyl 4'-heptylbiphenyl-4-carboxylate to the reaction with 4-hydroxy-2,2,6,6-tetramethylpiperidine; m.p. 106-107° C.

Example 15

1,2,2,6,6-Pentamethyl-4-[trans-4-(4-propylcyclohexyl) phenyl]piperidine was obtained in analogy to Skowronski et al., Pol. J. Chem. 54, 195, (1980) by reacting in tetrahydrofurane 1,2,2,6,6-pentamethyl-piperidine-4-one with the Grignard reagent prepared from 4-(trans-4-propylcyclohexyl)bromobenzene, subjecting the crude reaction product to azeotropic dehydration to 3,4-dehydro-1,2,2,6,6-pentamethyl-4-[trans-4-(4-propylcyclohexyl)phenyl]piperidine and hydrogenation in tetrahydrofuran, catalyzed by Pd/C, at ambient temperature and atmospheric pressure, followed by silica treatment, as a viscous liquid. $^1$H-NMR (300 MHz, CDCl$_3$/DMSO/TMS) δ=7.18 m, 4H), 2.65-2.49 (m, 2H), 2.24 (s, 3H), 1.95-1.80 (m, 6H), 1.55-1.15 (m, 9H), 1.12-0.96 (m, 14H), 0.91 (t, 3H)

Table 2 summarizes the results—(achieved with the equipment and procedure of examples 1 to 6) obtained by adding small quantities of several types of (I) to one of the following S$_c$ mixtures:

M1 {achiral block mixture based on 5-alkyl-2-(4-alkyloxyphenyl)pyrimidines}

M2 (chiral mixture based on derivatives of phenylpyrimidines)

M3b (achiral multi-component mixture based on ester and ether derivatives of phenylpyrimidines, fluorinated bi- and terphenyls and sulfur heterocycles)

M3 (like M3b, but chiral dopant added)

TABLE 2

| example | condition | mixture | storage 0 hrs | storage 100 hrs | storage 200 hrs | storage 300 hrs | storage 500 hrs |
|---|---|---|---|---|---|---|---|
| reference. | 20 V, 5 Hz | M1 | <0.01 | 0.3 | 0.35 | 0.48 | 0.25 |
| 16 | 20 V, 5 Hz | M1 + 5% expl. 13 | <0.01 | <0.01 | <0.01 | <0.01 | <0.01 |
| reference. | 20 V, 5 Hz | M3b | 0.21 | 4.69 | 4.36 | 4.37 | 4.32 |
| 17 | 20 V, 5 Hz | M3b + 0.1% expl. 13 | 0.17 | 0.3 | 0.48 | 0.47 | 0.54 |
| 18 | 20 V, 5 Hz | M3b + 0.2% expl. 13 | 0.08 | 0.23 | 0.23 | 0.25 | 0.27 |
| 19 | 20 V, 5 Hz | M3b + 0.4% expl. 13 | 0.16 | 0.23 | 0.2 | 0.22 | 0.25 |
| reference. | 5 V, 0.1 Hz | M4 | 0 | 2.56 | 7.57 | 3.48 | 6.33 |
| 20 | 5 V, 0.1 Hz | M4 + 0.4% expl. 13 | <0.01 | <0.01 | 0.12 | 0.22 | 0.17 |
| reference. | 5 V, 0.1 Hz | M2 | 0.2 | 8.18 | 10.93 | 9.49 | 6.43 |
| 21 | 5 V, 0.1 Hz | M2 + 0.4% expl. 13 | <0.01 | <0.01 | 0.08 | 0.48 | 0.73 |
| 22 | 5 V, 0.1 Hz | M2 + 0.2% expl. 14 | <0.01 | 1.76 | 2.37 | 2.08 | 1.87 |
| 23 | 5 V, 0.1 Hz | M2 + 0.4% expl. 14 | <0.01 | 1.14 | 1.57 | 1.41 | no data |
| 24 | 5 V, 0.1 Hz | M4 + 0.2% expl. 14 | <0.01 | 1.91 | 2.71 | 2.79 | 2.94 |
| 25 | 5 V, 0.1 Hz | M4 + 0.4% expl. 14 | <0.01 | 2.02 | 2.80 | 3.09 | 2.91 |

As can be seen by comparing with the respective reference examples {comprising no (I)}, the mixtures according to invention surprisingly exhibit a substantially lower ion content [$nC/cm^2$] over a longer period of time.

The invention claimed is:

1. A liquid crystal mixture comprising a compound of formula (I)

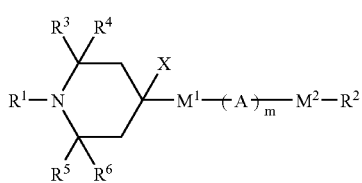

(I)

wherein $R^1$ is H or a linear or branched alkyl group of 1 to 20 C atoms, or a linear or branched alkenyl group of 2 to 20 C atoms, wherein in either case optionally one —$CH_2$— group is replaced by cyclohexylen-1,4-diyl, or one or two —$CH_2$— groups optionally are replaced by —O—, if non-adjacent to N, or by —C(=O)—, or —Si($CH_3$)$_2$—, and/or one or more H of the alkyl or alkenyl group optionally is replaced by F or $CH_3$;

$R^2$ stands for a) F, b) a linear or branched alkyl group of 1 to 20 C atoms, or a linear or branched alkenyl group of 2 to 20 C atoms, wherein in either case one or two —$CH_2$— groups optionally are replaced by —O—, —C(=O)O—, or —Si($CH_3$)$_2$—, and/or one or more H of the alkyl or alkenyl group is replaced by F or $CH_3$, c) a radical

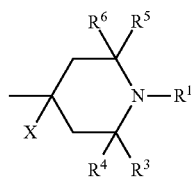

wherein independently from the respective meanings in (I) $R^3$, $R^4$, $R^5$, $R^6$ are, independently from another, an alkyl group of 1 to 8 C atoms;

$M^1$, $M^2$ represent, independently from another, a single bond, —OC(=O)—, —C(=O)O—, —$OCH_2$—, or —NH—;

A is i) —C(=Y)—, wherein Y is CH—Z, wherein Z is phenylen-1,4-diyl, optionally substituted by one to three halogen atoms, alkyl or alkyloxy groups of 1 to 4 C atoms, with the proviso that $M^1$ and $M^2$ are —C(=O)O— and —OC(=O)—, ii) —CHY—, wherein Y is $CH_2$—Z, wherein Z is phenylen-1,4-diyl, optionally substituted by one to three halogen atoms, alkyl or alkyloxy groups of 1 to 4 C atoms, with the proviso that $M^1$ and $M^2$ are —C(=O)O— and —OC(=O)—, iii)

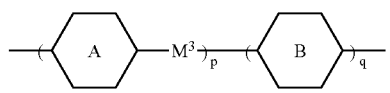

wherein p and q are 0, 1 or 2, wherein the sum of p+q is 1;

$M^3$ is a single bond or —OC(=O)—, —C(=O)O—, —$OCH_2$—, —$CH_2O$—, —C≡C—, —$CH_2CH_2$—, or —$CH_2CH_2CH_2CH_2$—;

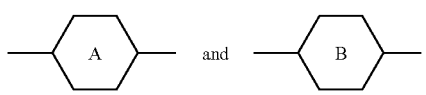

are, independently from another, phenylen-1,4-diyl, which is optionally substituted by one, two or three F, or cyclohexan-1,4-diyl, which is optionally substituted by one CN, CH$_3$ or F, or pyrimidin-2,5-diyl, which is optionally substituted by one F, pyridine-2,5-diyl, which is optionally substituted by one F, or naphthalene-2,6-diyl, which is optionally substituted by one, two or three F, or 1,2,3,4-tetrahydronaphthalene-2,6-diyl, wherein the aromatic ring is optionally substituted by one, two or three F, or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol,2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl;

X is H, OH, a linear or branched alkyl or alkyloxy group of 1 to 20 C atoms, wherein one or two —CH$_2$— groups are optionally replaced by —O—, —C(=O)O—, or —Si(CH$_3$)$_2$—, and optionally one or more H are replaced by F or CH$_3$; and m is 0 or 1; or X and M$^1$-(A)$_m$-M$^2$-R$^2$ together are
a) a ring of 4 to 16 members, optionally substituted by an alkyl radical of 1 to 15 C atoms,
b) a combination of two either directly linked or spiro-linked rings of, independently from another, 4 to 16 members, optionally substituted by an alkyl radical of 1 to 15 C atoms, wherein the rings, independently from another, are carbocycles or carbocycles comprising B, N, O or S heteroatoms.

2. A liquid crystal mixture according to claim 1, comprising 0.01 wt.-% to 10 wt.-% of one or several compounds of formula (I).

3. A liquid crystal mixture comprising a compound of formula (IV)

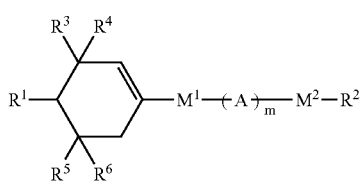

(IV)

wherein
R$^1$ is H or a linear or branched alkyl group of 1 to 20 C atoms, or a linear or branched alkenyl group of 2 to 20 C atoms, wherein in either case optionally one —CH$_2$— group is replaced by cyclohexylen-1,4-diyl, or one or two —CH$_2$-groups optionally are replaced by —O—, if non-adjacent to N, or by —C(=O)—, or —Si(CH$_3$)$_2$—, and/or one or more H of the alkyl or alkenyl group optionally is replaced by F or CH$_3$;
R$^2$ stands for
a) H or F,
b) a linear or branched alkyl group of 1 to 20 C atoms, or a linear or branched alkenyl group of 2 to 20 C atoms, wherein in either case one or two —CH$_2$— groups optionally are replaced by —O—, —C(=O)O—, or —Si(CH$_3$)$_2$—, and/or one or more H of the alkyl or alkenyl group is replaced by F or CH$_3$,
c) a radical

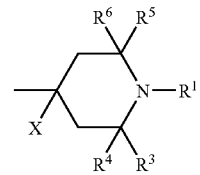

wherein independently from the respective meanings in (I) R$^3$, R$^4$, R$^5$, R$^6$ are, independently from another, an alkyl group of 1 to 8 C atoms;
M$^2$ represents a single bond, —OC(=O)—, —C(=O)O—, —OCH$_2$—, or —NH—;
A is
a) a linear or branched alkan-α,ω-diyl group of 1 to 20 C atoms or alkene-α,ω-diyl group of 2 to 20 C atoms, optionally, if non-adjacent to M$^1$ and M$^2$, one or two non-adjacent —CH$_2$— groups are replaced by —O—, or
b)

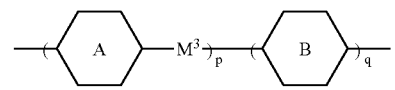

wherein
p and q are 0, 1 or 2, wherein the sum of p+q is 1;
M$^3$ is a single bond or —OC(=O)—, —C(=O)O—, —OCH$_2$—, —CH$_2$O—, —C≡C—, —CH$_2$CH$_2$—, or —CH$_2$CH$_2$CH$_2$CH$_2$—;

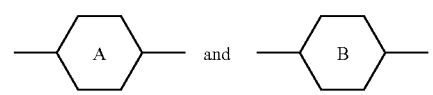

are, independently from another, phenylen-1,4-diyl, which is optionally substituted by one, two or three F, or cyclohexan-1,4-diyl, which is optionally substituted by one CN, CH$_3$ or F, or pyrimidin-2,5-diyl, which is optionally substituted by one F, pyridine-2,5-diyl, which is optionally substituted by one F, or naphthalene-2,6-diyl, which is optionally substituted by one, two or three F, or 1,2,3,4-tetrahydronaphthalene-2,6-diyl, wherein the aromatic ring is optionally substituted by one, two or three F, or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol,2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl;

X is H, OH, a linear or branched alkyl or alkyloxy group of 1 to 20 C atoms, wherein one or two —CH$_2$— groups are optionally replaced by —O—, —C(=O)O—, or —Si(CH$_3$)$_2$—, and optionally one or more H are replaced by F or CH$_3$;

m is 0 or 1; and

M¹ is a single bond.

4. A liquid crystal mixture according to claim 1, further comprising one or several antioxidants.

5. A liquid crystal mixture according to claim 4, wherein the mixture comprises 0.01 to 10 wt.-% of one or several antioxidants.

6. A liquid crystal mixture according to claim 4, further comprising one or several UV-stabilizers.

7. A liquid crystal mixture according to claim 1, which is chiral smectic.

8. A liquid crystal display device comprising a liquid crystal mixture according to claim 1.

9. A liquid crystal display device according to claim 8, wherein the device is operated in an active-matrix panel.

10. A liquid crystal display device according to claim 8, wherein the liquid crystal mixture is chiral smectic.

11. A liquid crystal display device according to claim 8, wherein the display is a monostable display.

12. A liquid crystal mixture according to claim 1, comprising a compound of the following formula

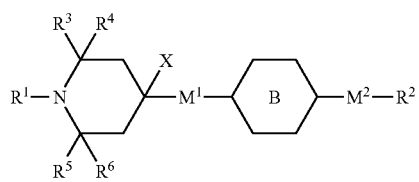
(Ib)

wherein

X is H;

R¹ is H or alkyl of 1 to 4 C atoms; and

R³, R⁴, R⁵, R⁶ are CH₃.

13. A liquid crystal mixture according to claim 1, comprising a compound of the following formula

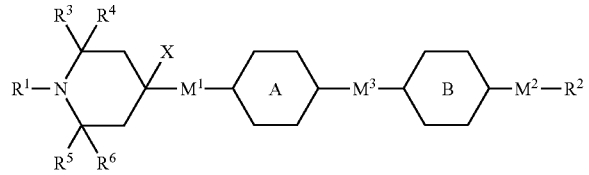
(Ic)

wherein

X is H;

R¹ is H or alkyl of 1 to 4 C atoms; and

R³, R⁴, R⁵, R⁶ are CH₃.

14. A liquid crystal mixture according to claim 1, comprising a compound of the following formula

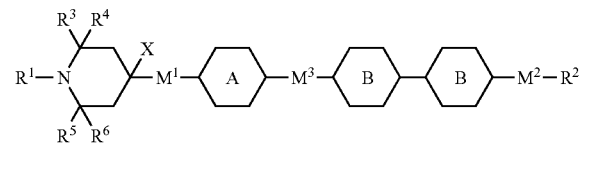
(Id)

wherein

X is H;

R¹ is H or alkyl of 1 to 4 C atoms; and

R³, R⁴, R⁵, R⁶ are CH₃.

15. A liquid crystal mixture according to claim 1, comprising a compound of the following formula

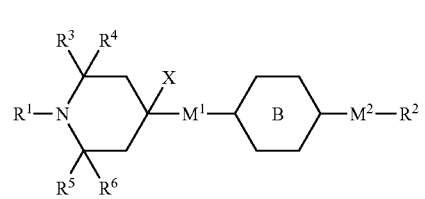
(Ib1)

wherein

X is H;

R¹ is H or alkyl of 1 to 4 C atoms;

R³, R⁴, R⁵, R⁶ are CH₃;

R² is H or an alkyl or alkoxy group of 1 to 16 C atoms, wherein one or two —CH₂— groups are optionally replaced by —O—, —OC(=O)— or —Si(CH₃)₂—, and optionally one or more H is replaced by F or CH₃;

M¹ is —OC(=O)—;

M² is a single bond; and

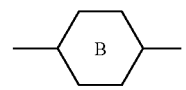

is phenylen-1,4-diyl, which is optionally substituted by one or two F, or is cyclohexylen-1,4-diyl, or pyrimidine-2,5-diyl, or pyridine-2,5-diyl.

16. A liquid crystal mixture according to claim 1, comprising a compound of the following formula

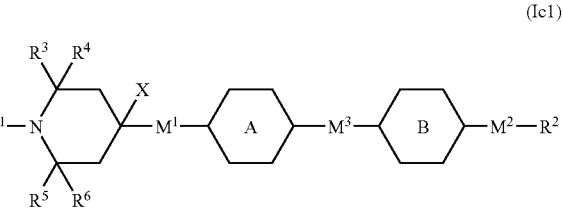
(Ic1)

wherein

X is H;

R¹ is H or alkyl of 1 to 4 C atoms;

R³, R⁴, R⁵, R⁶ are CH₃;

R² is H or an alkyl or alkoxy group of 1 to 16 C atoms, wherein one or two —CH₂— groups are optionally replaced by —O—, —OC(=O)— or —Si(CH₃)₂—, and optionally one or more H is replaced by F or CH₃;

M¹ is —OC(=O)—;

M² is a single bond;

M³ is a single bond, —OC(=O)—, or —OCH₂—;

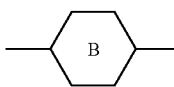

is phenylen-1,4-diyl, which is optionally substituted by one or two F, or is cyclohexylen-1,4-diyl, pyrimidine-2,5-diyl, or pyridine-2,5-diyl; and

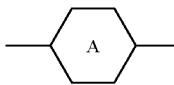

is phenylen-1,4-diyl, which is optionally substituted by one or two F, or is cyclohexylen-1,4-diyl, pyrimidine-2,5-diyl, or pyridine-2,5-diyl.

17. A liquid crystal mixture according to claim 1, which has a nematic phase.

18. A liquid crystal mixture according to claim 1, further comprising a compound of formula (IV)

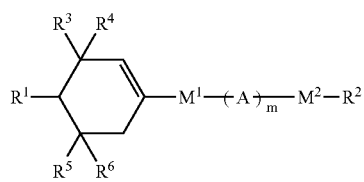

(IV)

wherein $R^1$ is H or a linear or branched alkyl group of 1 to 20 C atoms, or a linear or branched alkenyl group of 2 to 20 C atoms, wherein in either case optionally one —$CH_2$— group is replaced by cyclohexylen-1,4-diyl, or one or two —$CH_2$-groups optionally are replaced by —O—, if non-adjacent to N, or by —C(=O)—, or —Si$(CH_3)_2$—, and/or one or more H of the alkyl or alkenyl group optionally is replaced by F or $CH_3$;

$R^2$ stands for a) H or F, b) a linear or branched alkyl group of 1 to 20 C atoms, or a linear or branched alkenyl group of 2 to 20 C atoms, wherein in either case one or two —$CH_2$— groups optionally are replaced by —O—, —C(=O)O—, or —Si$(CH_3)_2$—, and/or one or more H of the alkyl or alkenyl group is replaced by F or $CH_3$, c) a radical

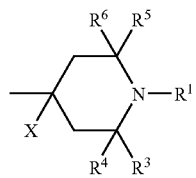

wherein independently from the respective meanings in (I) $R^3$, $R^4$, $R^5$, $R^6$ are, independently from another, an alkyl group of 1 to 8 C atoms;

$M^2$ represents a single bond, —OC(=O)—, —C(=O)O—, —OCH$_2$—, or —NH—;

A is a) a linear or branched alkan-α,ω-diyl group of 1 to 20 C atoms or alkene-α,ω-diyl group of 2 to 20 C atoms, optionally, if non-adjacent to $M^1$ and $M^2$, one or two non-adjacent —$CH_2$— groups are replaced by —O—, or b)

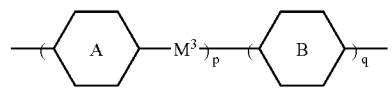

wherein p and q are 0, 1 or 2, wherein the sum of p+q is 1;

$M^3$ is a single bond or —OC(=O)—, —C(=O)O—, —OCH$_2$—, —CH$_2$O—, —C≡C—, —CH$_2$CH$_2$—, or —CH$_2$CH$_2$CH$_2$CH$_2$—;

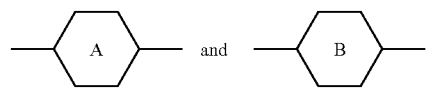

are, independently from another, phenylen-1,4-diyl, which is optionally substituted by one, two or three F, or cyclohexan-1,4-diyl, which is optionally substituted by one CN, $CH_3$ or F, or pyrimidin-2,5-diyl, which is optionally substituted by one F, pyridine-2,5-diyl, which is optionally substituted by one F, or naphthalene-2,6-diyl, which is optionally substituted by one, two or three F, or 1,2,3,4-tetrahydronaphthalene-2,6-diyl, wherein the aromatic ring is optionally substituted by one, two or three F, or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol,2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl;

X is H, OH, a linear or branched alkyl or alkyloxy group of 1 to 20 C atoms, wherein one or two —$CH_2$— groups are optionally replaced by —O—, —C(=O)O—, or —Si$(CH_3)_2$—, and optionally one or more H are replaced by F or $CH_3$;

m is 0 or 1; and $M^1$ is a single bond.

19. A liquid crystal mixture according to claim 1, further comprising a compound of formula (II)

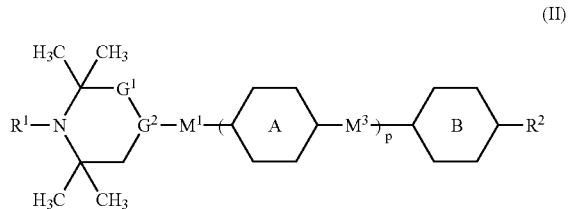

(II)

wherein $R^1$ is H or alkyl of 1 to 12 C atoms;

$R^2$ is H, a linear or branched alkyl group of 1 to 16 C atoms, or linear or branched alkenyl group of 2 to 16 C atoms, wherein in either case one —CH₂— group is optionally replaced by —O—, and optionally one or more H are replaced by F;
M¹ is —OC(=O)— or a single bond;
M³ is a single bond;
G¹-G² is —CH₂—CH— or —CH=C—;
p is 0 or 1;

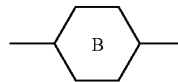

is phenylen-1,4-diyl, which is optionally substituted by one or two F, cyclohexylen-1,4-diyl, biphenyl-4,4'-diyl, which is optionally substituted by one or two F per ring, 1,1'-cyclohexylphenyl-4,4'-diyl, wherein the phenyl moiety is optionally substituted by one or two F, or 1,1'-phenylcyclohexyl-4,4'-diyl, wherein the phenyl moiety is optionally substituted by one or two F, or 1,1'-bicyclohexyl-4,4'-diyl;

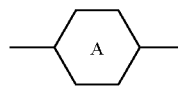

is phenylen-1,4-diyl, which is optionally substituted by one or two F, or cyclohexylen-1,4-diyl,
with the provisos that
a) R² is H only in case p is 1;
b) if p is 0, than R² is a linear or branched alkyl group of 1 to 16 C atoms or linear or branched alkenyl group of 2 to 16 C atoms and

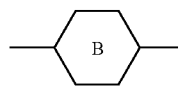

is cyclohexylen-1,4-diyl; and
c) -G¹-G²- can be —CH=C— only in the case M¹ is a single bond.

20. A liquid crystal mixture according to claim 1, further comprising a compound of formula (III)

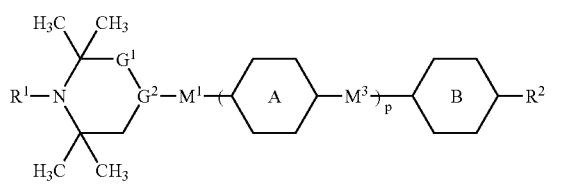

(III)

wherein
R¹ is H or alkyl of 1 to 12 C atoms;
R² is H, a linear or branched alkyl group of 1 to 16 C atoms, or linear or branched alkenyl group of 2 to 16 C atoms, wherein in either case one —CH₂— group is optionally replaced by —O—, and optionally one or more H are replaced by F;
M¹ is —OC(=O)— or a single bond;
M³ is a single bond;

G¹-G² is —CH₂—CH— or —CH=C—;
p is 0 or 1;

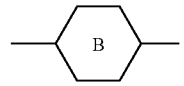

is pyrimidin-2,5-diyl, pyridin-2,5-diyl, which is optionally ortho to N substituted by F, phenylen-1,4-diyl, which is optionally substituted by one or two F, or cyclohexylen-1,4-diyl, biphenyl-4,4'-diyl, which is optionally substituted by one or two F per ring, 1,1'-cyclohexylphenyl-4,4'-diyl, wherein the phenyl moiety is optionally substituted by one or two F, or 1,1'-phenylcyclohexyl-4,4'-diyl, wherein the phenyl moiety is optionally substituted by one or two F, or 1,1'-bicyclohexyl-4,4'-diyl;

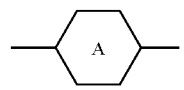

is phenylen-1,4-diyl, which is optionally substituted by one or two F, cyclohexylen-1,4-diyl, biphenyl-4,4'-diyl, which is optionally substituted by one or two F per ring, 1,1'-cyclohexylphenyl-4,4'-diyl, wherein the phenyl moiety is optionally substituted by one or two F, or 1,1'-phenylcyclohexyl-4,4'-diyl, wherein the phenyl moiety is optionally substituted by one or two F, or 1,1'-bicyclohexyl-4,4'-diyl, pyrimidin-2,5-diyl, or pyridin-2,5-diyl, which is optionally ortho to N substituted by F,
with the provisos that
a) one and only one of

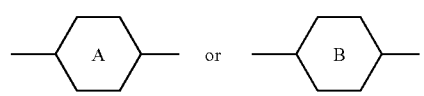

is pyrimidin-2,5-diyl or pyridine-2,5-diyl, which is optionally ortho to N substituted by F; and
b) -G¹-G² can be —CH=C— only in case M¹ is a single bond.

21. A compound of formula (I), (II), (III), or (IV)

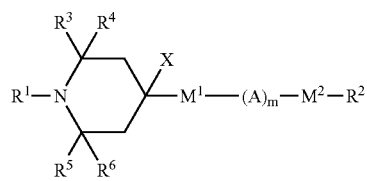

(I)

wherein
R¹ is H or a linear or branched alkyl group of 1 to 20 C atoms, or a linear or branched alkenyl group of 2 to 20 C atoms, wherein in either case optionally one —CH₂— group is replaced by cyclohexylen-1,4-diyl, or one or two —CH₂— groups optionally are replaced by —O—, if non-adjacent to N, or by —C(=O)—, or —Si(CH₃)₂—, and/or one or more H of the alkyl or alkenyl group optionally is replaced by F or CH₃;

$R^2$ stands for a radical

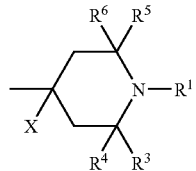

wherein independently from the respective meanings in (I)
$R^3$, $R^4$, $R^5$, $R^6$ are, independently from another, an alkyl group of 1 to 8 C atoms;
$M^1$ represents a single bond, —OCH$_2$—, or —NH—;
$M^2$ represents —C(=O)O—;
A is

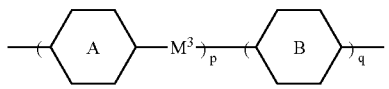

wherein
p and q are 0, 1 or 2, wherein the sum of p+q is 1;
$M^3$ is a single bond or —OC(=O)—, —C(=O)O—, —OCH$_2$—, —CH$_2$O—, —C≡C—, —CH$_2$CH$_2$—, or —CH$_2$CH$_2$CH$_2$CH$_2$—;

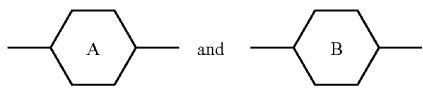

are, independently from another, phenylen-1,4-diyl, which is optionally substituted by one, two or three F, or cyclohexan-1,4-diyl, which is optionally substituted by one CN, CH$_3$ or F, or pyrimidin-2,5-diyl, which is optionally substituted by one F, pyridine-2,5-diyl, which is optionally substituted by one F, or naphthalene-2,6-diyl, which is optionally substituted by one, two or three F, or 1,2,3,4-tetrahydronaphthalene-2,6-diyl, wherein the aromatic ring is optionally substituted by one, two or three F, or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol,2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl;
X is H, OH, a linear or branched alkyl or alkyloxy group of 1 to 20 C atoms, wherein one or two —CH$_2$— groups are optionally replaced by —O—, —C(=O)O—, or —Si(CH$_3$)$_2$—, and optionally one or more H are replaced by F or CH$_3$; and
m is 1; or
X and $M^1$-(A)$_m$-$M^2$-$R^2$ together are
a) a ring of 4 to 16 members, optionally substituted by an alkyl radical of 1 to 15 C atoms,
b) a combination of two either directly linked or spiro-linked rings of, independently from another, 4 to 16 members, optionally substituted by an alkyl radical of 1 to 15 C atoms, wherein the rings, independently from another, are carbocycles or carbocycles comprising B, N, O or S heteroatoms;

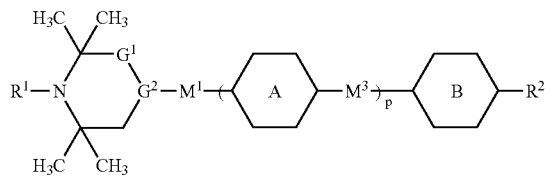

wherein
$R^1$ is H or alkyl of 1 to 12 C atoms;
$R^2$ is H, a linear or branched alkyl group of 1 to 16 C atoms, or linear or branched alkenyl group of 2 to 16 C atoms, wherein in either case one —CH$_2$— group is optionally replaced by —O—, and optionally one or more H are replaced by F;
$M^1$ is —OC(=O)— or a single bond;
$M^3$ is a single bond;
$G^1$-$G^2$ is —CH$_2$—CH— or —CH=C—;
p is 0 or 1;

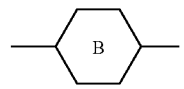

is phenylen-1,4-diyl, which is optionally substituted by one or two F, cyclohexylen-1,4-diyl, biphenyl-4,4'-diyl, which is optionally substituted by one or two F per ring, 1,1'-cyclohexylphenyl-4,4'-diyl, wherein the phenyl moiety is optionally substituted by one or two F, or 1,1'-phenylcyclohexyl-4,4'-diyl, wherein the phenyl moiety is optionally substituted by one or two F, or 1,1'-bicyclohexyl-4,4'-diyl;

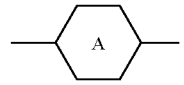

is phenylen-1,4-diyl, which is optionally substituted by one or two F, or cyclohexylen-1,4-diyl,
with the provisos that
a) $R^2$ is H only in case p is 1;
b) if p is 0, then $R^2$ is a linear or branched alkyl group of 1 to 16 C atoms or linear or branched alkenyl group of 2 to 16 C atoms and

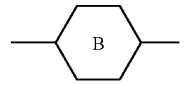

is cyclohexylen-1,4-diyl; and
c) -$G^1$-$G^2$- can be —CH=C— only in the case $M^1$ is a single bond;

(III)

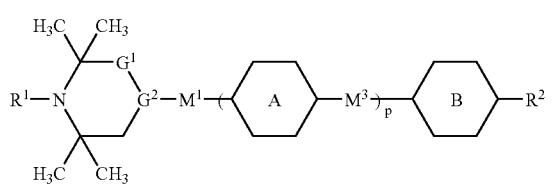

wherein
R¹ is H or alkyl of 1 to 12 C atoms;
R² is H, a linear or branched alkyl group of 1 to 16 C atoms, or linear or branched alkenyl group of 2 to 16 C atoms, wherein in either case one —CH₂— group is optionally replaced by —O—, and optionally one or more H are replaced by F;
M¹ is —OC(=O)— or a single bond;
M³ is a single bond;
G¹-G² is —CH₂—CH— or —CH=C—;
p is 0 or 1;

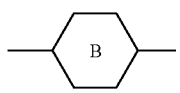

is pyrimidin-2,5-diyl, pyridin-2,5-diyl, which is optionally ortho to N substituted by F, phenylen-1,4-diyl, which is optionally substituted by one or two F, or cyclohexylen-1,4-diyl, biphenyl-4,4'-diyl, which is optionally substituted by one or two F per ring, 1,1'-cyclohexylphenyl-4,4'-diyl, wherein the phenyl moiety is optionally substituted by one or two F, or 1,1'-phenylcyclohexyl-4,4'-diyl, wherein the phenyl moiety is optionally substituted by one or two F, or 1,1'-bicyclohexyl-4,4'-diyl;

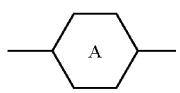

is phenylen-1,4-diyl, which is optionally substituted by one or two F, cyclohexylen-1,4-diyl, biphenyl-4,4'-diyl, which is optionally substituted by one or two F per ring, 1,1'-cyclohexylphenyl-4,4'-diyl, wherein the phenyl moiety is optionally substituted by one or two F, or 1,1'-phenylcyclohexyl-4,4'-diyl, wherein the phenyl moiety is optionally substituted by one or two F, or 1,1'-bicyclohexyl-4,4'-diyl, pyrimidin-2,5-diyl, or pyridin-2,5-diyl, which is optionally ortho to N substituted by F,
with the provisos that
a) one and only one of

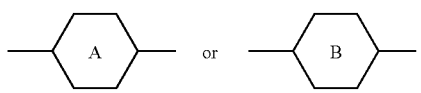

is pyrimidin-2,5-diyl or pyridine-2,5-diyl, which is optionally ortho to N substituted by F; and
b) -G¹-G² can be —CH=C— only in case M¹ is a single bond;

(IV)

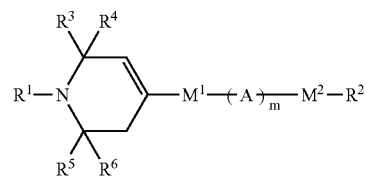

wherein
R¹ is H or a linear or branched alkyl group of 1 to 20 C atoms, or a linear or branched alkenyl group of 2 to 20 C atoms, wherein in either case optionally one —CH₂— group is replaced by cyclohexylen-1,4-diyl, or one or two —CH₂-groups optionally are replaced by —O—, if non-adjacent to N, or by —C(=O)—, or —Si(CH₃)₂—, and/or one or more H of the alkyl or alkenyl group optionally is replaced by F or CH₃;
R² stands for
a radical

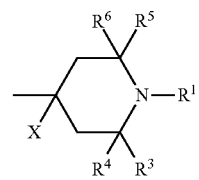

wherein independently from the respective meanings in (I) R³, R⁴, R⁵, R⁶ are, independently from another, an alkyl group of 1 to 8 C atoms;
M² represents a single bond, —OC(=O)—, or —C(=O)O—;
A is

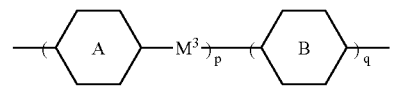

wherein
p and q are 0, 1 or 2, wherein the sum of p+q is 1;
M³ is a single bond or —OC(=O)—, —C(=O)O—, —OCH₂—, —CH₂O—, —C≡C—, —CH₂CH₂—, or —CH₂CH₂CH₂CH₂—;

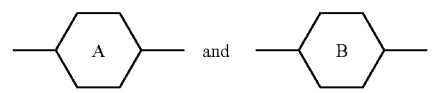

are, independently from another, phenylen-1,4-diyl, which is optionally substituted by one, two or three F, or cyclohexan-1,4-diyl, which is optionally substituted by one CN, CH₃ or F, or pyrimidin-2,5-diyl, which is optionally substituted by one F, pyridine-2,5-diyl, which is optionally substituted by one F, or naphthalene-2,6-diyl, which is optionally substituted by one, two or three F, or 1,2,3,4-tetrahydronaphthalene-2,6-diyl, wherein the aromatic ring is optionally substituted by one, two or three F, or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol,2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl;

X is H, OH, a linear or branched alkyl or alkyloxy group of 1 to 20 C atoms, wherein one or two —CH$_2$— groups are optionally replaced by —O—, —C(=O)O—, or —Si(CH$_3$)$_2$—, and optionally one or more H are replaced by F or CH$_3$;

m is 1; and

M$^1$ is a single bond.

22. A compound according to claim 21, which is a compound of formula (II), (III), or (IV).

23. A compound of formula (I) or (IV)

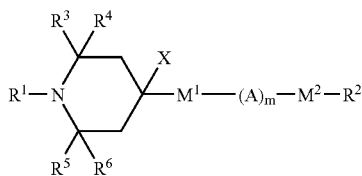

(I)

wherein

R$^1$ is H or a linear or branched alkyl group of 1 to 20 C atoms, or a linear or branched alkenyl group of 2 to 20 C atoms, wherein in either case optionally one —CH$_2$— group is replaced by cyclohexylen-1,4-diyl, or one or two —CH$_2$— groups optionally are replaced by —O—, if non-adjacent to N, or by —C(=O)—, or —Si(CH$_3$)$_2$—, and/or one or more H of the alkyl or alkenyl group optionally is replaced by F or CH$_3$;

R$^2$ stands for
a) F,
b) a linear or branched alkyl group of 1 to 20 C atoms, or a linear or branched alkenyl group of 2 to 20 C atoms, wherein in either case one or two —CH$_2$— groups optionally are replaced by —O—, —C(=O)O—, or —Si(CH$_3$)$_2$—, and/or one or more H of the alkyl or alkenyl group is replaced by F or CH$_3$,
c) a radical

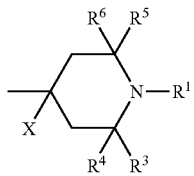

wherein independently from the respective meanings in (I) R$^3$, R$^4$, R$^5$, R$^6$ are, independently from another, an alkyl group of 1 to 8 C atoms;

M$^1$ represents —OCH$_2$— or —NH—;
M$^2$ represents —OC(=O)—, —C(=O)O— or —NH—;
A is

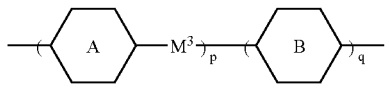

wherein
p and q are 0, 1 or 2, wherein the sum of p+q is 1;
M$^3$ is a single bond or —OC(=O)—, —C(=O)O—, —OCH$_2$—, —CH$_2$O—, —C≡C—, —CH$_2$CH$_2$—, or —CH$_2$CH$_2$CH$_2$CH$_2$—;

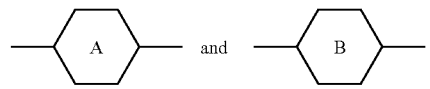

are, independently from another, phenylen-1,4-diyl, which is optionally substituted by one, two or three F, or cyclohexan-1,4-diyl, which is optionally substituted by one CN, CH$_3$ or F, or pyrimidin-2,5-diyl, which is optionally substituted by one F, pyridine-2,5-diyl, which is optionally substituted by one F, or naphthalene-2,6-diyl, which is optionally substituted by one, two or three F, or 1,2,3,4-tetrahydronaphthalene-2,6-diyl, wherein the aromatic ring is optionally substituted by one, two or three F, or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol,2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl;

X is H, OH, a linear or branched alkyl or alkyloxy group of 1 to 20 C atoms, wherein one or two —CH$_2$— groups are optionally replaced by —O—, —C(=O)O—, or —Si(CH$_3$)$_2$—, and optionally one or more H are replaced by F or CH$_3$; and m is 0 or 1; or X and M$^1$-(A)$_m$-M$^2$-R$^2$ together are
a) a ring of 4 to 16 members, optionally substituted by an alkyl radical of 1 to 15 C atoms,
b) a combination of two either directly linked or spirolinked rings of, independently from another, 4 to 16 members, optionally substituted by an alkyl radical of 1 to 15 C atoms, wherein the rings, independently from another, are carbocycles or carbocycles comprising B, N, O or S heteroatoms;
or

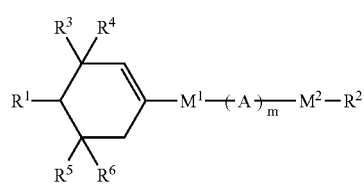

(IV)

wherein
R$^1$ is H or a linear or branched alkyl group of 1 to 20 C atoms, or a linear or branched alkenyl group of 2 to 20 C atoms, wherein in either case optionally one —CH$_2$— group is replaced by cyclohexylen-1,4-diyl, or one or two —CH$_2$-groups optionally are replaced by —O—, if non-adjacent to N, or by —C(=O)—, or —Si(CH$_3$)$_2$—, and/or one or more H of the alkyl or alkenyl group optionally is replaced by F or CH$_3$;

R² stands for
a) F,
b) a linear or branched alkyl group of 1 to 20 C atoms, or a linear or branched alkenyl group of 2 to 20 C atoms, wherein in either case one or two —CH₂— groups optionally are replaced by —C(=O)O—, or —Si(CH₃)₂—, and/or one or more H of the alkyl or alkenyl group is replaced by F or CH₃,
c) a radical

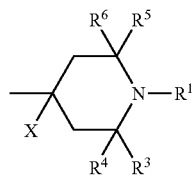

wherein independently from the respective meanings in (I)
R³, R⁴, R⁵, R⁶ are, independently from another, an alkyl group of 1 to 8 C atoms;
M² represents a single bond, or —C(=O)O—;
A is

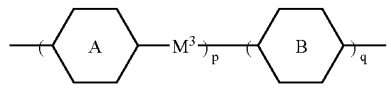

wherein
p and q are 0, 1 or 2, wherein the sum of p+q is 1;
M³ is a single bond or —OC(=O)—, —C(=O)O—, —OCH₂—, —CH₂O—, —C≡C—, —CH₂CH₂—, or —CH₂CH₂CH₂CH₂—;

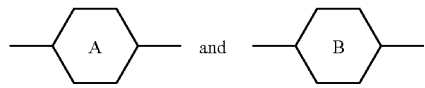

are, independently from another, phenylen-1,4-diyl, which is optionally substituted by one, two or three F, or cyclohexan-1,4-diyl, which is optionally substituted by one CN, CH₃ or F, or pyrimidin-2,5-diyl, which is optionally substituted by one F, pyridine-2,5-diyl, which is optionally substituted by one F, or naphthalene-2,6-diyl, which is optionally substituted by one, two or three F, or 1,2,3,4-tetrahydronaphthalene-2,6-diyl, wherein the aromatic ring is optionally substituted by one, two or three F, or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol,2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl;
X is H, OH, a linear or branched alkyl or alkyloxy group of 1 to 20 C atoms, wherein one or two —CH₂—groups are optionally replaced by —O—, —C(=O)O—, or —Si(CH₃)₂—, and optionally one or more H are replaced by F or CH₃;
m is 1; and
M¹ is a single bond.

24. A compound of formula (I) or (IV)

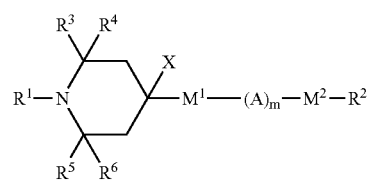

(I)

wherein
R¹ is H or a linear or branched alkyl group of 1 to 20 C atoms, or a linear or branched alkenyl group of 2 to 20 C atoms, wherein in either case optionally one —CH₂— group is replaced by cyclohexylen-1,4-diyl, or one or two —CH₂— groups optionally are replaced by —O—, if non-adjacent to N, or by —C(=O)—, or —Si(CH₃)₂—, and/or one or more H of the alkyl or alkenyl group optionally is replaced by F or CH₃;
R² stands for
a) F,
b) a linear or branched alkyl group of 1 to 20 C atoms, or a linear or branched alkenyl group of 5 to 20 C atoms, wherein in either case one or two —CH₂— groups optionally are replaced by —Si(CH₃)₂—, and/or one or more H of the alkyl or alkenyl group is replaced by F or CH₃,
c) a radical

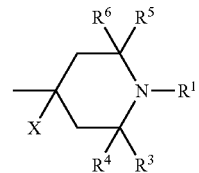

wherein independently from the respective meanings in (I)
R³, R⁴, R⁵, R⁶ are, independently from another, an alkyl group of 1 to 8 C atoms;
M¹ represents —OCH₂—, or —NH—, and M² represents —NH—, and if A denotes —C(=Y)— or —CHY—, then M¹ and M² represent —C(=O)O— and —OC(=O)—, respectively;
A is

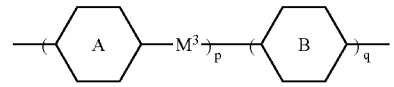

wherein
p and q are 0, 1 or 2, wherein the sum of p+q is 1;
M³ is a single bond or —OC(=O)—, —C(=O)O—, —OCH₂—, —CH₂O—, —C≡C—, —CH₂CH₂—, or —CH₂CH₂CH₂CH₂—;

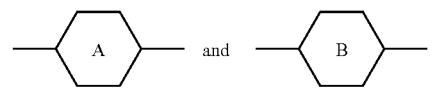

are, independently from another, phenylen-1,4-diyl, which is optionally substituted by one, two or three F, or cyclohexan-1,4-diyl, which is optionally substituted by one CN, CH$_3$ or F, or pyrimidin-2,5-diyl, which is optionally substituted by one F, pyridine-2,5-diyl, which is optionally substituted by one F, or naphthalene-2,6-diyl, which is optionally substituted by one, two or three F, or 1,2,3,4-tetrahydronaphthalene-2,6-diyl, wherein the aromatic ring is optionally substituted by one, two or three F, or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol,2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl;

X is H, OH, a linear or branched alkyl or alkyloxy group of 1 to 20 C atoms, wherein one or two —CH$_2$— groups are optionally replaced by —O—, —C(=O)O—, or —Si(CH$_3$)$_2$—, and optionally one or more H are replaced by F or CH$_3$; and m is 1; or X and M$^1$-(A)$_m$-M$^2$-R$^2$ together are a) a ring of 4 to 16 members, optionally substituted by an alkyl radical of 1 to 15 C atoms, b) a combination of two either directly linked or spiro-linked rings of, independently from another, 4 to 16 members, optionally substituted by an alkyl radical of 1 to 15 C atoms, wherein the rings, independently from another, are carbocycles or carbocycles comprising B, N, O or S heteroatoms, or

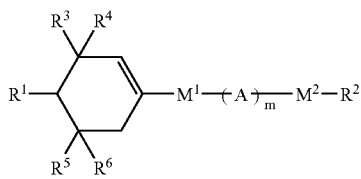
(IV)

wherein

R$^1$ is H or a linear or branched alkyl group of 1 to 20 C atoms, or a linear or branched alkenyl group of 2 to 20 C atoms, wherein in either case optionally one —CH$_2$— group is replaced by cyclohexylen-1,4-diyl, or one or two —CH$_2$-groups optionally are replaced by —O—, if non-adjacent to N, or by —C(=O)—, or —Si(CH$_3$)$_2$—, and/or one or more H of the alkyl or alkenyl group optionally is replaced by F or CH$_3$;

R$^2$ stands for a) F, b) a linear or branched alkyl group of 1 to 20 C atoms, or a linear or branched alkenyl group of 5 to 20 C atoms, wherein in either case one or two —CH$_2$— groups optionally are replaced by —C(=O)O—, or —Si(CH$_3$)$_2$—, and/or one or more H of the alkyl or alkenyl group is replaced by F or CH$_3$, c) a radical

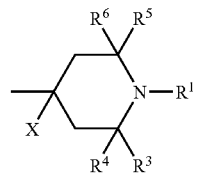

wherein independently from the respective meanings in (I) R$^3$, R$^4$, R$^5$, R$^6$ are, independently from another, an alkyl group of 1 to 8 C atoms;

M$^1$ is a single bond;

M$^2$ represents a single bond, —OC(=O)—, or —C(=O)O—;

if A denotes —C(=Y)— or —CHY—, then M$^1$ and M$^2$ represent —C(=O)O— and —OC(=O)—, respectively;

A is i) —C(=Y)—, wherein Y is CH—Z, wherein Z is phenylen-1,4-diyl, optionally substituted by one to three halogen atoms, alkyl or alkyloxy groups of 1 to 4 C atoms, with the proviso that M$^1$ and M$^2$ are —C(=O)O— and —OC(=O)—, respectively, ii) —CHY—, wherein Y is CH$_2$—Z, wherein Z is phenylen-1,4-diyl, optionally substituted by one to three halogen atoms, alkyl or alkyloxy groups of 1 to 4 C atoms, with the proviso that M$^1$ and M$^2$ are —C(=O)O— and —OC(=O)—, respectively, iii)

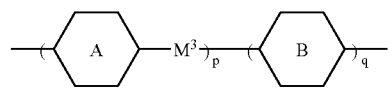

wherein p and q are 0, 1 or 2, wherein the sum of p+q is 1;

M$^3$ is a single bond or —OC(=O)—, —C(=O)O—, —OCH$_2$—, —CH$_2$O—, —C≡C—, —CH$_2$CH$_2$—, or —CH$_2$CH$_2$CH$_2$CH$_2$—;

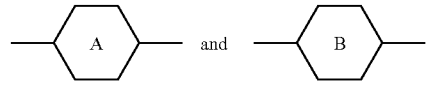

are, independently from another, phenylen-1,4-diyl, which is optionally substituted by one, two or three F, or cyclohexan-1,4-diyl, which is optionally substituted by one CN, CH$_3$ or F, or pyrimidin-2,5-diyl, which is optionally substituted by one F, pyridine-2,5-diyl, which is optionally substituted by one F, or naphthalene-2,6-diyl, which is optionally substituted by one, two or three F, or 1,2,3,4-tetrahydronaphthalene-2,6-diyl, wherein the aromatic ring is optionally substituted by one, two or three F, or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol,2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl;

X is H, OH, a linear or branched alkyl or alkyloxy group of 1 to 20 C atoms, wherein one or two —CH$_2$— groups are optionally replaced by —O—, —C(=O)O—, or —Si(CH$_3$)$_2$—, and optionally one or more H are replaced by F or CH$_3$; and m is 1.

25. A compound of formula (I) or (IV) of claim 24, wherein

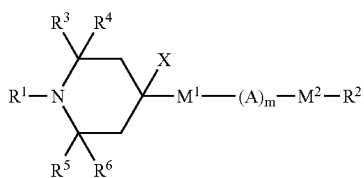 (I)

wherein

R$^1$ is H or a linear or branched alkyl group of 1 to 20 C atoms, or a linear or branched alkenyl group of 2 to 20 C atoms, wherein in either case optionally one —CH$_2$— group is replaced by cyclohexylen-1,4-diyl, or one or two —CH$_2$— groups optionally are replaced by —O—, if non-adjacent to N, or by —C(=O)—, or —Si(CH$_3$)$_2$—, and/or one or more H of the alkyl or alkenyl group optionally is replaced by F or CH$_3$;

R$^2$ stands for a) F b) a linear or branched alkyl group of 1 to 20 C atoms, wherein one or two —CH$_2$— groups optionally are replaced by —Si(CH$_3$)$_2$—, and/or one or more H of the alkyl group is replaced by F or CH$_3$, c) a radical

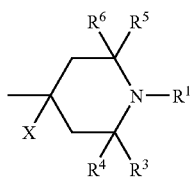

wherein independently from the respective meanings in (I)

R$^3$, R$^4$, R$^5$, R$^6$ are, independently from another, an alkyl group of 1 to 8 C atoms;

M$^1$ represents —OCH$_2$—, or —NH—, and M$^2$ represents —NH—, and if A denotes —C(=Y)— or —CHY—, then M$^1$ and M$^2$ represent —C(=O)O— and —OC(=O)—, respectively;

A is

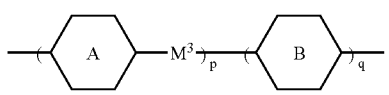

wherein p and q are 0, 1 or 2, wherein the sum of p+q is 1;

M$^3$ is a single bond or —OC(=O)—, —C(=O)O—, —OCH$_2$—, —CH$_2$O—, —C≡C—, —CH$_2$CH$_2$—, or —CH$_2$CH$_2$CH$_2$CH$_2$—;

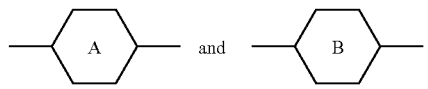

are, independently from another, phenylen-1,4-diyl, which is optionally substituted by one, two or three F, or cyclohexan-1,4-diyl, which is optionally substituted by one CN, CH$_3$ or F, or pyrimidin-2,5-diyl, which is optionally substituted by one F, pyridine-2,5-diyl, which is optionally substituted by one F, or naphthalene-2,6-diyl, which is optionally substituted by one, two or three F, or 1,2,3,4-tetrahydronaphthalene-2,6-diyl, wherein the aromatic ring is optionally substituted by one, two or three F, or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol,2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl;

X is H, OH, a linear or branched alkyl or alkyloxy group of 1 to 20 C atoms, wherein one or two —CH$_2$— groups are optionally replaced by —O—, —C(=O)O—, or —Si(CH$_3$)$_2$—, and optionally one or more H are replaced by F or CH$_3$; and m is 1; or X and M$^1$-(A)$_m$-M$^2$-R$^2$ together are a) a ring of 4 to 16 members, optionally substituted by an alkyl radical of 1 to 15 C atoms, b) a combination of two either directly linked or spiro-linked rings of, independently from another, 4 to 16 members, optionally substituted by an alkyl radical of 1 to 15 C atoms, wherein the rings, independently from another, are carbocycles or carbocycles comprising B, N, O or S heteroatoms, or

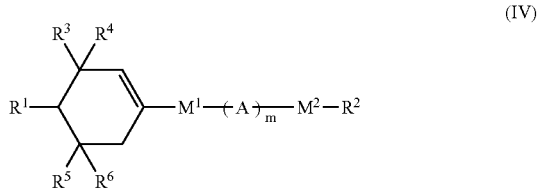 (IV)

wherein

R$^1$ is H or a linear or branched alkyl group of 1 to 20 C atoms, or a linear or branched alkenyl group of 2 to 20 C atoms, wherein in either case optionally one —CH$_2$— group is replaced by cyclohexylen-1,4-diyl, or one or two —CH$_2$-groups optionally are replaced by —O—, if non-adjacent to N, or by —C(=O)—, or —Si(CH$_3$)$_2$—, and/or one or more H of the alkyl or alkenyl group optionally is replaced by F or CH$_3$;

R$^2$ stands for a) F, b) a linear or branched alkyl group of 1 to 20 C atoms, wherein one or two —CH$_2$— groups optionally are replaced by —C(=O)O—, or —Si(CH$_3$)$_2$—, and/or one or more H of the alkyl group is replaced by F or CH$_3$, c) a radical

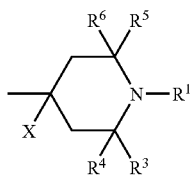

wherein independently from the respective meanings in (I)
$R^3$, $R^4$, $R^5$, $R^6$ are, independently from another, an alkyl group of 1 to 8 C atoms;
$M^1$ is a single bond;
$M^2$ represents a single bond, —OC(═O)—, or —C(═O)O—;
if A denotes —C(═Y)— or —CHY—, then $M^1$ and $M^2$ represent —C(═O)O— and —OC(═O)—, respectively;
A is
i) —C(═Y)—, wherein Y is CH—Z, wherein Z is phenylen-1,4-diyl, optionally substituted by one to three halogen atoms, alkyl or alkyloxy groups of 1 to 4 C atoms, with the proviso that $M^1$ and $M^2$ are —C(═O)O— and —OC(═O)—, respectively,
ii) —CHY—, wherein Y is $CH_2$—Z, wherein Z is phenylen-1,4-diyl, optionally substituted by one to three halogen atoms, alkyl or alkyloxy groups of 1 to 4 C atoms, with the proviso that $M^1$ and $M^2$ are —C(═O)O— and —OC(═O)—, respectively,
iii)

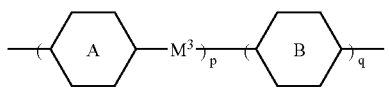

wherein
p and q are 0, 1 or 2, wherein the sum of p+q is 1;
$M^3$ is a single bond or —OC(═O)—, —C(═O)O—, —OCH$_2$—, —CH$_2$O—, —C≡C—, —CH$_2$CH$_2$—, or —CH$_2$CH$_2$CH$_2$CH$_2$—;

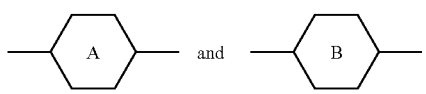

are, independently from another, phenylen-1,4-diyl, which is optionally substituted by one, two or three F, or cyclohexan-1,4-diyl, which is optionally substituted by one CN, $CH_3$ or F, or pyrimidin-2,5-diyl, which is optionally substituted by one F, pyridine-2,5-diyl, which is optionally substituted by one F, or naphthalene-2,6-diyl, which is optionally substituted by one, two or three F, or 1,2,3,4-tetrahydronaphthalene-2,6-diyl, wherein the aromatic ring is optionally substituted by one, two or three F, or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol,2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl;

X is H, OH, a linear or branched alkyl or alkyloxy group of 1 to 20 C atoms, wherein one or two —CH$_2$— groups are optionally replaced by —O—, —C(═O)O—, or —Si(CH$_3$)$_2$—, and optionally one or more H are replaced by F or $CH_3$; and
m is 1.

26. A compound of claim 21, which is of formula (IV), wherein
$R^1$ is a linear or branched alkyl group of 1 to 20 C atoms, or a linear or branched alkenyl group of 2 to 20 C atoms, wherein in either case one —CH$_2$— group is replaced by cyclohexylen-1,4-diyl,
and/or one or more H of the alkyl or alkenyl group optionally is replaced by F or $CH_3$.

27. A compound of claim 21, which is of formula (IV), wherein
$R^2$ stands for a radical

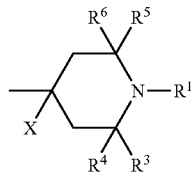

wherein independently from the respective meanings in (I)
$R^1$ is H or a linear or branched alkyl group of 1 to 20 C atoms, or a linear or branched alkenyl group of 2 to 20 C atoms, wherein in either case optionally one —CH$_2$— group is replaced by cyclohexylen-1,4-diyl, or one or two —CH$_2$— groups optionally are replaced by —O—, if non-adjacent to N, or by —C(═O)—, or —Si(CH$_3$)$_2$—, and/or one or more H of the alkyl or alkenyl group optionally is replaced by F or $CH_3$;
$R^3$, $R^4$, $R^5$, $R^6$ are, independently from another, an alkyl group of 1 to 8 C atoms; and
X is H, OH, a linear or branched alkyl or alkyloxy group of 1 to 20 C atoms, wherein one or two —CH$_2$— groups are optionally replaced by —O—, —C(═O)O—, or —Si(CH$_3$)$_2$—, and optionally one or more H are replaced by F or $CH_3$.

28. A compound of claim 21, which is of formula (IV), wherein
A is

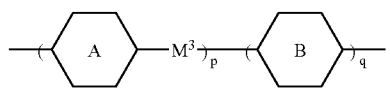

wherein
p and q are 0, 1 or 2, wherein the sum of p+q is 1;
$M^3$ is a single bond or —OC(═O)—, —C(═O)O—, —OCH$_2$—, —CH$_2$O—, —C≡C—, —CH$_2$CH$_2$—, or —CH$_2$CH$_2$CH$_2$CH$_2$—; and

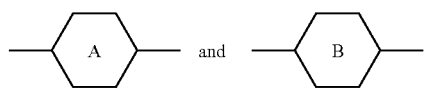

are, independently from another, phenylen-1,4-diyl, which is optionally substituted by one, two or three F, or cyclohexan-1,4-diyl, which is optionally substituted by one CN, CH₃ or F, or pyrimidin-2,5-diyl, which is optionally substituted by one F, pyridine-2,5-diyl, which is optionally substituted by one F, or naphthalene-2,6-diyl, which is optionally substituted by one, two or three F, or 1,2,3,4-tetrahydronaphthalene-2,6-diyl, wherein the aromatic ring is optionally substituted by one, two or three F, or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol,2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl.

29. A compound of claim 23, which is of formula (IV), wherein
R² is a linear or branched alkyl group of 2 to 20 C atoms, or a linear or branched alkenyl group of 2 to 20 C atoms, wherein in either case one or two —CH₂— groups optionally are replaced by —C(=O)O—, or —Si(CH₃)₂—, and/or one or more H of the alkyl or alkenyl group is replaced by F or CH₃,
or F
or a radical

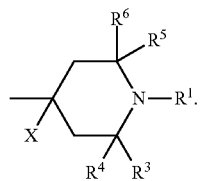

30. A compound of formula (IV),

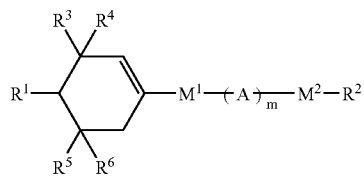

(IV)

wherein
R¹ is H or a linear or branched alkyl group of 1 to 20 C atoms, or a linear or branched alkenyl group of 2 to 20 C atoms, wherein in either case optionally one —CH₂— group is replaced by cyclohexylen-1,4-diyl, or one or two —CH₂-groups optionally are replaced by —O—, if non-adjacent to N, or by —C(=O)—, or —Si(CH₃)₂—, and/or one or more H of the alkyl or alkenyl group optionally is replaced by F or CH₃;
R² is a linear or branched alkyl group of 2 to 20 C atoms, or a linear or branched alkenyl group of 5 to 20 C atoms, wherein in either case one or two —CH₂-groups optionally are replaced by —Si(CH₃)₂—, and/or one or more H of the alkyl or alkenyl group is replaced by F or CH₃,
or F
or a radical

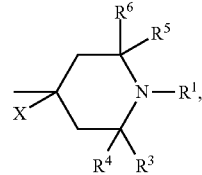

R³, R⁴, R⁵, R⁶ are, independently from another, an alkyl group of 1 to 8 C atoms;
M² represents a single bond, —OC(=O)—, or —C(=O)O—;
A is

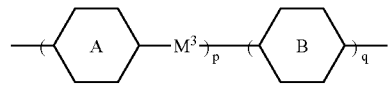

wherein
p and q are 0, 1 or 2, wherein the sum of p+q is 1;
M³ is a single bond or —OC(=O)—, —C(=O)O—, —OCH₂—, —CH₂O—, —C≡C—, —CH₂CH₂—, or —CH₂CH₂CH₂CH₂—;

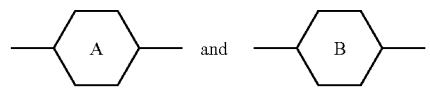

are, independently from another, phenylen-1,4-diyl, which is optionally substituted by one, two or three F, or cyclohexan-1,4-diyl, which is optionally substituted by one CN, CH₃ or F, or pyrimidin-2,5-diyl, which is optionally substituted by one F, pyridine-2,5-diyl, which is optionally substituted by one F, or naphthalene-2,6-diyl, which is optionally substituted by one, two or three F, or 1,2,3,4-tetrahydronaphthalene-2,6-diyl, wherein the aromatic ring is optionally substituted by one, two or three F, or decahydronaphthalene-2,6-diyl, or indane-2,5(6)-diyl, or fluorene-2,7-diyl, or phenanthrene-2,7-diyl, or 9,10-dihydrophenanthrene-2,7-diyl, or (1,3,4)thiadiazol-2,5-diyl, or (1,3)thiazol,2,5-diyl, or (1,3)thiazol-2,4-diyl, or thiophen-2,4-diyl, or thiophen-2,5-diyl, or (1,3)dioxan-2,5-diyl, or piperidin-1,4-diyl, or piperazin-1,4-diyl;
X is H, OH, a linear or branched alkyl or alkyloxy group of 1 to 20 C atoms, wherein one or two —CH₂— groups are optionally replaced by —O—, —C(=O)O—, or —Si(CH₃)₂—, and optionally one or more H are replaced by F or CH₃;
m is 1; and
M¹ is a single bond.

* * * * *